US010500420B2

(12) United States Patent
Grady et al.

(10) Patent No.: US 10,500,420 B2
(45) Date of Patent: Dec. 10, 2019

(54) SMALL BEAM AREA, MID-VOLTAGE RADIOTHERAPY SYSTEM WITH REDUCED SKIN DOSE, REDUCED SCATTER AROUND THE TREATMENT VOLUME, AND IMPROVED OVERALL ACCURACY

(71) Applicants: John K. Grady, Ayer, MA (US); Lim Cheung, Ayer, MA (US)

(72) Inventors: John K. Grady, Ayer, MA (US); Lim Cheung, Ayer, MA (US)

(*) Notice: Subject to any disclaimer, the term of this patent is extended or adjusted under 35 U.S.C. 154(b) by 624 days.

(21) Appl. No.: 15/163,826

(22) Filed: May 25, 2016

(65) Prior Publication Data
US 2016/0310763 A1    Oct. 27, 2016

Related U.S. Application Data

(63) Continuation-in-part of application No. 14/494,264, filed on Sep. 23, 2014.

(60) Provisional application No. 61/881,274, filed on Sep. 23, 2013, provisional application No. 62/166,167, filed on May 26, 2015.

(51) Int. Cl.
*A61N 5/10* (2006.01)
*A61B 6/03* (2006.01)
*A61B 6/06* (2006.01)
*A61B 6/00* (2006.01)

(52) U.S. Cl.
CPC .......... *A61N 5/1081* (2013.01); *A61B 6/032* (2013.01); *A61B 6/06* (2013.01); *A61B 6/4435* (2013.01); *A61N 5/1047* (2013.01); *A61N 5/1082* (2013.01); *A61N 5/1084* (2013.01); *A61N 2005/1091* (2013.01); *A61N 2005/1095* (2013.01)

(58) Field of Classification Search
CPC ........................................................ A61N 5/10
See application file for complete search history.

(56) References Cited

U.S. PATENT DOCUMENTS

| | | |
|---|---|---|
| 2,890,349 A | 6/1959 | Laszlo |
| 3,892,967 A | 7/1975 | Grady et al. |
| 5,008,907 A | 4/1991 | Norman et al. |
| 5,515,416 A | 5/1996 | Siczek et al. |
| 5,661,773 A | 8/1997 | Swerdloff et al. |
| 6,728,335 B1 | 4/2004 | Thomson et al. |
| 6,789,941 B1 | 9/2004 | Grady |
| 7,068,754 B2 | 6/2006 | Goebel et al. |
| 7,188,999 B2 | 3/2007 | Mihara et al. |
| 7,583,775 B2 | 9/2009 | Ozaki |
| 7,594,751 B2 | 9/2009 | Grebner et al. |

(Continued)

OTHER PUBLICATIONS

Keller et al., Experimental Measurement of Radiological Penumbra Associated With Intermediate Energy X-Rays (1 MV) and Small Radiosurgery Field Sizes, Med Phys 34 (10), Oct. 2007.

(Continued)

*Primary Examiner* — Thomas R Artman
(74) *Attorney, Agent, or Firm* — Pandiscio & Pandiscio

(57) ABSTRACT

A radiotherapy system comprising an X-ray tube operating at 100 to 800 kVp for providing X-ray beams of 50 mm diameter or less (and preferably approximately 30 mm or less) and configured to move the entrance beam footprint on the body during irradiation to any arbitrary sequential position set that has been predetermined to limit the intervening tissue dose rate at any one location to a safe level, such that the sum of the skin area traversed during treatment is 20 to 100 times the beam area.

16 Claims, 21 Drawing Sheets

(56) References Cited

U.S. PATENT DOCUMENTS

| | | |
|---|---|---|
| 7,620,147 B2 | 11/2009 | Gertner et al. |
| 8,059,874 B2 | 11/2011 | Pfister et al. |
| 8,280,001 B2 | 10/2012 | Wang et al. |
| 9,308,395 B2 | 4/2016 | Adler, Jr. et al. |
| 2013/0144104 A1 | 6/2013 | Adler, Jr. et al. |
| 2015/0190658 A1 | 7/2015 | Yu |
| 2015/0217136 A1 | 8/2015 | Stanescu et al. |
| 2015/0231413 A1 | 8/2015 | Grady |
| 2016/0310763 A1 | 10/2016 | Grady et al. |

OTHER PUBLICATIONS

Keller et al., Intermediate Energy Photons (1 MV) to Improve Dose Gradient, Conformality, and Homogeneity: Potential Benefits for Small Field Intracranial Radiosurgery,Med. Phys. 36 (33), Jan. 2009.

Pignol et al., Electron and Photon Spread Contributions to the Radiological Penumbra for Small Monoenergetic X-Ray Beam (< 2 MeV), Journal of Applied Physics 105, 102011, 2009, Amercan Institute of Physics.

Selman, Basic Physics of Radiation Therapy, 1960, pp. 430-438.

Selman, Basic Physics of Radiation Therapy, 1960, Therapy Planning, pp. 214-243.

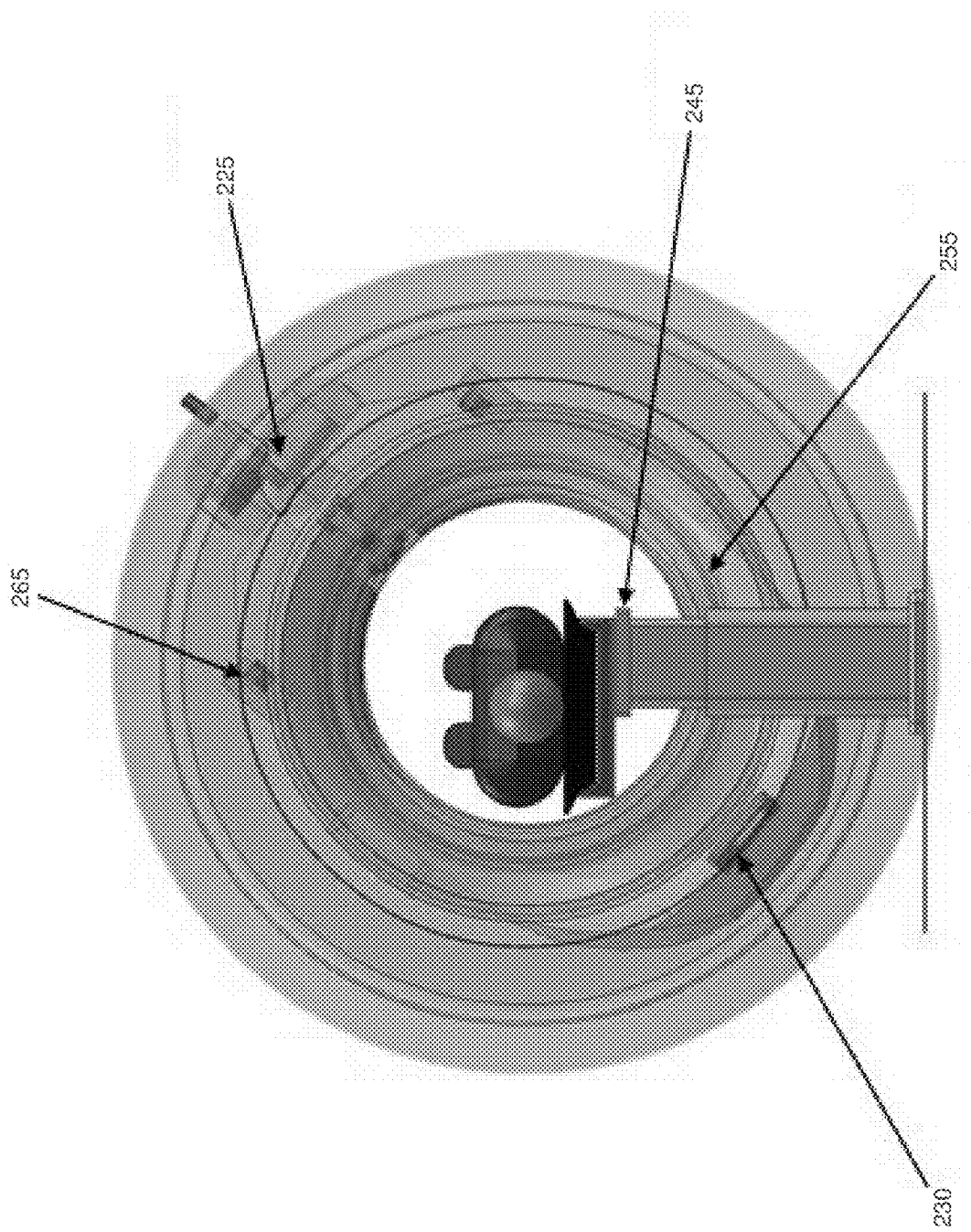

SMALL BEAM AREA, MID-VOLTAGE RADIOTHERAPY SYSTEM WITH REDUCED SKIN DOSE, REDUCED SCATTER AROUND THE TREATMENT VOLUME, AND IMPROVED OVERALL ACCURACY

REFERENCE TO PENDING PRIOR PATENT APPLICATIONS

This patent application:

(i) is a continuation-in-part of pending prior U.S. patent application Ser. No. 14/494,264, filed Sep. 23, 2014 by John K. Grady for SMALL BEAM AREA, MID-VOLTAGE RADIOTHERAPY SYSTEM WITH REDUCED SKIN DOSE, REDUCED SCATTER AROUND THE TREATMENT VOLUME, AND IMPROVED OVERALL ACCURACY, which in turn claims benefit of prior U.S. Provisional Patent Application Ser. No. 61/881,274, filed Sep. 23, 2013 by John K. Grady for SMALL BEAM AREA, MID-VOLTAGE RADIOTHERAPY SYSTEM WITH REDUCED SKIN DOSE, REDUCED SCATTER AROUND THE TREATMENT VOLUME, AND IMPROVED OVERALL ACCURACY; and (ii) claims benefit of pending prior U.S. Provisional Patent Application Ser. No. 62/166,167, filed May 26, 2015 by John K. Grady et al. for METHOD FOR IMAGE GUIDED RADIATION THERAPY.

The three (3) above-identified patent applications are hereby incorporated herein by reference.

FIELD OF THE INVENTION

This invention relates to medical apparatus and procedures in general, and more particularly to systems for providing radiation therapy to a patient and use of the same.

BACKGROUND OF THE INVENTION

Radiation therapy has been used for many years to treat a patient by radiating selected anatomy so as to destroy tumors and the like.

Starting in the 1930's and continuing into the 1970's, "orthovoltage" X-ray therapy units of approximately 300 kVp/1.2 mm copper (Cu) half-value layer (HVL) were widely used to treat malignancies (e.g., tumors). The word "orthovoltage" was based on the concept of "the right energy", in the sense that a 300 kVp electrical potential, resulting in an approximately 160 keV X-ray beam, generates a photon energy such that the skin absorption and the bone absorption becomes approximately equal, which is a necessity for radiotherapy treatments within the skull, and an advantage for radiotherapy treatments elsewhere in the body. Energies lower than approximately 160 keV will deposit energy preferentially in bone. In this respect it should be appreciated that Compton scatter of the radiation within the bone effectively concentrates the radiation dose in the vasculature of the bone, which can destroy the bone vasculature. Thus, energies below approximately 160 keV are generally detrimental to the bone.

The 300 kVp units used into the 1970's had the disadvantage of excessive skin dose delivery (e.g., when compared to the radiation dose which is actually delivered to tumors in the body, after taking into account the absorption of the radiation by intervening tissue). This is particularly true when the radiotherapy is delivered using 1, 2 or 3 fixed entrance "portals". In such a situation, the skin dose may be 3 to 5 times the tumor dose, and the skin is generally destroyed before the tumor is destroyed. Multiple fixed oversized entry portals, and multiple radiation sessions, were used as a partial solution to the problem of excessive skin dose delivery. However, it should be appreciated that the imaging of tumors at that time was comparatively crude, limited to perhaps 10 mm or so accuracy, and was severely hampered by the lack of precise knowledge of the tumor edges in three dimensions (3D). As a result, practitioners generally resorted to stationary multiple entrance portals, multiple radiation sessions and generally oversized beams to deal with the uncertainty of tumor location. The locations of the entry portals, and their sizes, were generally determined by "best effort" projections based on two dimension (2D) X-ray images. See Joseph Selman, MD, "Basic Physics of Radiation Therapy", 1960, "Therapy Planning" pp 214-243.

It was recognized that higher photon energies could be used to address the known fall-off in radiation intensity that occurs with depth, whereby to improve the efficacy of the radiation treatment and spare the skin from the aforementioned radiation overdose problem.

To this end, efforts were made to create higher energy X-ray tubes. However, the engineering problems associated with creating direct X-ray tubes over 300-400 kVp were substantial. Several 1 MeV units were built, however. These high energy X-ray tubes generally used Van de Graaf generators (see, for example, the work of High Voltage Engineering and Massachusetts Institute of Technology) or RF resonant systems (see, for example, the Maxitron systems of General Electric), and were often 20 to 30 feet long.

The 1 to 2 MeV X-ray systems based on Van de Graaf generators and/or RF resonance beams generally fell out of favor due to the difficulty of moving the X-ray beams in 3D (e.g., because of the large physical size of the X-ray source enclosure).

In the mid-1950's, the "Gamma Knife" system (e.g., of Leksell) introduced the idea of using multiple isocentric beams, at higher energy levels, to provide radiotherapy to the patient. More particularly, the Gamma Knife system provided hundreds of high energy (approximate 1.2 MeV) spherically-arrayed cobalt beams focused to an isocenter. These beams were (and are) poorly defined due to the large size of the cobalt source (typically tens of millimeters) and the short collimators which are inherent in the spherical array. This poor beam definition is problematic since sharp beam edges are necessary in order to avoid unintentionally radiating nearby healthy tissue. In addition, the Gamma Knife system provides stationary beams, and utilizes a fixed circular shape, thereby providing only spherical treatment volumes. Thus, the Gamma Knife system is unable to provide the variable, controllable treatment volumes necessary to closely match the shape of the anatomy (e.g., tumors) which is to be treated. In addition, the Gamma Knife system suffers from diffuse scatter of the primary beam, which is inherent in energy levels over about 1.2 MeV.

The 1.2 MeV cobalt systems, including the Gamma Knife systems, generally fell out of favor largely due to their relatively large cobalt radiation sources (typically tens of millimeters) which caused the edges of the radiation beam to be very poorly defined, even with good collimators. This is due to the simple geometric problems inherent in collimating a large (e.g., 20 mm) radiation source (see FIG. 1) versus collimating a small (e.g., 1 mm) radiation source (see FIG. 2). More particularly, FIG. 1 shows a typically large cobalt source 5 of about 20 mm size, such as is commonly used in the Gamma Knife system, being collimated by a collimator 10. As can be seen from FIG. 1, it is not possible to collimate such a large source to a sharp edge (see "large error" 15), thereby effectively eliminating any possibility of providing a sharp clinical edge to the radiation beam. FIG. 2, on the other hand, is a schematic view showing the sharp edge resulting from a 1 mm X-ray source (or focal spot) 20 as it is collimated by a collimator 25, and the resulting "small error" 30. Note that with the large cobalt source 5, the penumbra of the beam edge may take 10 mm or more to "fade out" radially, from the nominal or desired edge, thereby making the beam emitted by a large cobalt source effectively useless if the desired treatment beam is to be 10 mm or less. This is a significant problem, given the current interest in small, accurate treatment volumes enabled by accurate imaging.

Subsequently, there was developed the linear particle accelerator (Linac) systems which are common today. These Linac systems typically have an energy level of about 6 MeV, which makes them highly effective in addressing the known fall-off in radiation intensity with depth, thereby improving the efficacy of the radiation treatment and sparing the skin from radiation overdose. Although the secondary scatter envelope edge of a 6 MeV beam may be 4 to 5 times that of the early 300 kVp beams (due primarily to tissue scatter generated in vitro, and not beam geometry), the secondary scatter problem was of nominal consequence in the early days of Linacs due to the relatively low accuracy of tumor location which was common at the time. Note that in vitro tissue scatter of the radiation beam (which can reach 8-10 mm beyond the edge of a high energy radiation beam) cannot be suppressed by improved collimators.

Concurrent with the aforementioned improvements in radiotherapy systems, anatomical imaging systems have also been significantly improving, such that a 1 mm location accuracy is now routinely obtained. As a result, the X-ray beams can become smaller, and they can be more precisely positioned with the use of improved imaging modalities (e.g., CT, MRI and PET), or integral X-ray viewing.

As a result, the tissue scattering which is inherent in high energy beams such as the current 6 MeV Linac systems, and which was previously of less concern due to the relatively low accuracy of tumor location, has now become a considerable problem.

More particularly, the secondary scatter effects of a high energy beam causes a "scatter" or "fog" of radiation that may have a range of up to 8-10 mm outside of the actual geometric beam. See FIG. 3, which shows the significant radiation scatter which can occur within tissue when using a high energy (e.g., 6 MeV) beam, and FIG. 4, which shows the nominal beam scatter which can occur within tissue when using a low energy (e.g., 100 kVp-800 kVp) beam. More particularly, FIG. 3 is a schematic view showing a typical 6 MeV Linac beam generated from an X-ray source 35, with secondary radiation 40 (generated by scatter interactions within the body) extending out to the dotted line 45. This is approximately 10 mm away from the geometric beam, generating the "scatter error" 50. Thus, even with excellent beam collimation, a 6 MeV beam is significantly scattered in tissue, again preventing the achievement of a sharp edge. By comparison, FIG. 4 is a schematic view showing a 1.0 mm X-ray source 55, operating at 100-800 kVp so as to generate only short-range "Compton scatter" 60 as the major component of the scatter error and hence generating a sub-1 mm scatter error 65.

As noted above, the secondary scatter effects of a high energy (e.g., 6 MeV) beam did not present a significant problem with early Linac systems, inasmuch as tumor location was considerably less accurate than it is today, and inasmuch as the beams were fairly large and the gains in reducing excessive skin dose significantly outweighed "actual beam edge" definition drawbacks. It was accepted as the price of a large gain in efficacy and a significant reduction in skin damage. However, it is obviously a severe limit for the small, accurate beams desired in radiotherapy today. Others aware of these problems have recognized the medical physics at work here, and have outlined the potential benefits of "older" orthovoltage beams (e.g., 300 kVp beams) for higher net accuracy. See "Intermediate energy photons (1 MV) to improve dose gradient, conformality, and homogeneity: Potential benefits for small field intracranial radiosurgery", Brian M. Keller, et al, Med. Phys. 36 (1), January 2009, © 2009 Am. Assoc. Phys. Med.; "Electron and photon spread contributions to the radiological penumbra for small monoenergetic x-ray beam (≤2 MeV), Jean-Philippe Pignol, et al, Journal of Applied Physics 105, 102011 (2009), © 2009 American Institute of Physics; and "Experimental measurement of radiological penumbra associated with intermediate energy x-rays (1 MV) and small radiosurgery field sizes", Brian M. Keller, et al, Med Phys 34 (10), October 2007, © 2007 Am. Assoc. Phys. Med 3996.

A second major drawback associated with Linac systems, in particular for neuroradiosurgery, stems from the Linac's intended and historic advantage of high energy (and hence low fall-off as the beam travels within tissue). The high energy (e.g., 6 MeV) of the treatment beam causes the beam to continue on through the tissue at close to full destructive energy on the far side of the treatment zone, and the beam is increasing in diameter, and the "fog" of radiation still surrounds it, potentially wreaking havoc on normal tissue beyond or beside the treatment volume. This, combined with diffuse edges, pair production, and several other secondary effects associated with high energy beams, inherently limits what can be done to obtain a sharp beam edge at 6 MeV. By way of example but not limitation, with current Linac systems, even using multi-leaf collimators (2 to 3 mm are the smallest size that can work effectively) to tailor the 6 MeV beam, only 5 mm to 10 mm of beam precision is possible inside the body. This is ten times worse control than imaging accuracy would otherwise allow, and can prevent treatment of small lesions near critical anatomy such as the optic nerve.

Much of the recent prior art and current developments are geared to somehow gaining control of the Linac "fog of radiation" problems. See U.S. Pat. No. 8,280,001, issued Oct. 2, 2012 to Wang et al. From this comes the observation that it is pointless to make a multi-leaf, "fine grain" collimation system, capable of a 1 mm geometric beam formation, if scatter within the patient will still be 5 to 8 times greater than the 1 mm geometric beam.

The presented X-ray edge definition problem is somewhat analogous to the situation where a very fine line (e.g., less than 1 mm) is to be drawn on paper—the pen used to draw it must be sharp (i.e., also less than 1 mm).

SUMMARY OF THE INVENTION

It has occurred to the Applicant that the Orthovoltage (or mid-voltage) X-ray energy level provides this fine edge, inasmuch as essentially all tissue absorption is short-range Compton scattering; but to use this mid-voltage X-ray intensity clinically, for very small, accurate beams, a new approach is needed. In other words, Applicant has determined that properly applied mid-voltage beams (e.g., in the range of 100 kVp to 800 kVp) still possess very desirable inherent edge accuracy properties for radiotherapy or radiosurgery, despite the widespread (and perhaps incorrect)

opinion that mid-voltage beams are obsolete, and that "Linac is better". However, Applicant also recognizes that a new system level approach is needed to use these "mid-voltage" X-ray beams so as to obtain their advantages without encountering their disadvantages.

In particular, the present invention employs the concept of "critical limits" in defining how to use the considerable advantage of the all-Compton absorption of mid-voltage X-ray beams, leading to a closely-defined overall system for correctly applying mid-voltage beams to clinical problems.

The advantages of mid-voltage beams to be utilized, and their useful ranges in the new system approach follow, presented as critical limits to a clinically-useful mid-voltage system:

Critical Limit 1. For beams between 100 kVp and 800 kVp (i.e., a "mid-voltage" beam), the absorption process in tissue is almost entirely Compton absorption. This is well understood, and a nominal scatter range can be assigned to it, generally from sub-1 mm to 1 mm, dependent upon the energy of the beam, which then delivers a known accuracy to the beam edge. By comparison, the 6 MeV Linac system is characterized by an edge scatter or "fog" which is approximately 5 mm to 8 mm wide, due to the many non-Compton processes taking place in the tissue at 6 MeV. These non-Compton processes generate long-range scatter (which is essentially harmful radiation) which extends well outside the desired beam width. Therefore, the present invention preferably operates between 100 kVp and 800 kVp.

Critical Limit 2. Compton processes are up to 1.2 times as lethal to cells per Gy as non-Compton processes, although that also applies to any errant radiation. See Joseph Selman, MD, "Basic Physics of Radiation Therapy", 1960, pp 430-438. Therefore, close definition of the mid-voltage beam is essential, and this is achievable using a radiation source of small size, between approximately 0.6 mm and 3.0 mm diameter, and preferably between approximately 0.6 mm and 1.5 mm, and preferably approximately 1.0 mm diameter.

Critical Limit 3. It is possible to design an X-ray tube in the mid-voltage energy range, providing the intended small focal spot or source size (e.g., of only 1.0 mm or so), by using a shallow anode angle (e.g., less than 16 degrees, and preferably between 8 and 16 degrees).

By combining the foregoing Critical Limits 1, 2 and 3 (i.e., mid-voltage beam intensity with all-Compton absorption, close beam definition using a small source size, and beam generation via a shallow anode angle X-ray tube), with proper system geometry (e.g., a 660 mm source-to-tumor distance, and a multi-leaf collimator (MLC) made of 1.0 mm to 2.0 mm leafs or fingers, located approximately two-thirds of the 660 mm distance to the patient), a beam edge definition of about sub-1 mm to about 1 mm results, and is maintained inside the body. In general, it is desirable for the distance between the X-ray tube and the treatment volume to range between about 400 mm and about 750 mm.

Working with the foregoing, the problem still remains of the excessive skin dose delivery associated with mid-voltage X-ray beams, which is due to the more rapid beam intensity fall-off in tissue due to the higher absorption rate of a mid-voltage beam. In order to be clinically effective, the skin dose delivery must also be maintained within critical limits. Resolution of this problem is essential to the success of a medical radiotherapy application using sub-MeV energy. The present invention addresses this problem as follows.

In the case of neuroradiosurgery, a greatly simplified but "worst case" numerical example will be used to explain the unifying underlying operating concept of this new system that addresses skin dose and intensity fall-off within tissue.

The numerical descriptions which follow are only approximate due to many technical variables, but they are intended to be close to clinical values.

For small radiosurgical beams, one can envision a 15 mm beam width (i.e., about the size of a dime) to treat a 14 mm spherical tumor located "deep" within the brain. If that beam is stationary, and if the tumor is located 10 cm into the head, then for a 2 mm copper HVL (approximately 350 kVp), the radiation dose at the tumor is about 28 percent of the radiation dose at the dime-sized skin entrance portal. To make a truly worst-case scenario, a factor of one-fifth will be used (i.e., the radiation dose at the tumor is assumed to be about 20% of the radiation dose at the skin entrance portal). See Joseph Selman, MD, "Basic Physics of Radiation Therapy", 1960; also published depth/dose curves.

A typical lethal dose to the tumor volume might need to be 20 Gy; but applying more than 2 Gy to the skin has severe consequences. From the 5:1 drop-off ratio (i.e., skin dose: tumor dose) discussed above, a "worst case" total of 100 Gy must be "passed" through the skin portal in order to achieve the 20 Gy treatment dose on the deep-set tumor volume. If this is to be limited to 2 Gy at any one skin entrance portal (i.e., the desired maximum skin dose), there must be at least 50 different dime-sized entrance portals, with each entrance portal limited to 2 Gy each.

It is obvious that, in fact, 50 "dimes" will fit on the general hemisphere of a human skull, so requiring the use of 50 different skin entrance portals is plausible for the single session destruction of a tumor of the aforementioned size via radiosurgery. All beams remain sharply defined, since (i) a collimated, small diameter (e.g., 1 mm) radiation source is used, whereby to eliminate the edge definition issues associated with large radiation sources, and (ii) a mid-voltage (e.g., 100 kVp to 800 kVp) radiation source is used, whereby to provide minimal (i.e., Compton-only) scatter of the beam in the tissue. This approach improves beam accuracy and hence also improves clinical outcomes. In addition, and significantly, the exit dose (i.e., the dose imposed on tissue located on the far side of the tumor) is far lower with the mid-voltage beam than is the exit dose of Linac-based 6 MeV beams, due to the more rapid fall-off of mid-voltage beams in tissue, a major issue for head and neck treatments.

Thus, a significant aspect of the present invention is that the X-ray source and its associated collimator produce a small diameter beam, such that 50 or so skin entrance portals may be used to direct radiation at the treatment volume. In general, it is preferred that the X-ray beam be approximately 50 mm or less in diameter (and preferably approximately 30 mm or less in diameter). In one preferred form of the invention, the X-ray beam has a diameter of 15 mm. In another preferred form of the invention, the X-ray beam has a diameter between 2 mm and 25 mm, corresponding to the projected small tumor size.

It will be appreciated that the small diameter, well-defined mid-voltage X-ray beam may be directed to the treatment volume through the 50 or so skin entrance portals by delivering discrete X-ray dosages at each of the skin entrance portals or by scanning a continuously-emitting X-ray source across the range of skin entrance portals; of course, for higher keV or other geometries, less than 50 portals will suffice. By way of example but not limitation, use of a 600 kVp source may improve the situation by a factor of 2, i.e., 25 entrance portals may suffice where 50 entrance portals were required for a 300 kVp source.

More particularly, in one form of the invention, the X-ray beam may be directed to the treatment volume by positioning the X-ray source in line with one skin entrance portal and then activating the X-ray source so as to deliver therapeutic radiation to the treatment volume while limiting harmful radiation to the skin (e.g., delivering approximately 0.4 Gy to the treatment volume and no more than 2 Gy to the skin). Then the X-ray source is moved so as to be in line with another (e.g., adjacent) skin portal and radiation is delivered to the treatment volume. This process is continued until the appropriate treatment dose has been delivered to the treatment volume.

Alternatively, and more preferably, in another form of the invention, the X-ray beam may be directed to the treatment volume by scanning a continuously-emitting X-ray source across the range of skin entrance portals so as to deliver therapeutic radiation to the treatment volume while limiting harmful radiation to the skin (e.g., delivering approximately 20 Gy to the treatment volume and no more than 2 Gy to any one skin entrance portal).

The actual location of the 50 (or 25, etc.) different entrance portals (i.e., the "50 dimes", "25 dimes", etc.) is set by a medical planning protocol, taking into account what tissue is to be radiated and what tissue is to be avoided. Preferably this protocol is effected through the use of computerized, 3D dose planning software, which will be apparent to those skilled in the art in view of the present disclosure. Significantly, this dose planning software can take advantage of the sharp edge definition, and rapid fall-off, of the mid-voltage beam.

It will be appreciated that the exact number of different entrance portals utilized is a function of the location of the treatment volume, the intervening tissue, the strength of the X-ray beam, the width of the X-ray beam, etc. In general, the net area of the entrance track for the X-ray beam (i.e., the sum of all of the different skin entrance portals) is approximately 20 to 100 times the beam area at a given skin entrance portal.

It should be appreciated that the mid-voltage beams may be circular in cross-section, or they may be non-circular in cross-section, or they may be dynamically shaped through the use of multi-leaf collimators (MLC), e.g., with 1-2 mm leafs, wherein the shaping of the beams is dictated by the tumor shape in any given projection (e.g., using CT data for any given projection).

The advantage of a mid-voltage beam having closely-defined edges remains throughout the procedure, as the angle of projection of the beam, and its cross-sectional configuration (adjusted by varying the MLC apertures) change to radiate a given projection or view.

There is, therefore, adjustability to the angle of projection of the closely-defined beam, and to the cross-sectional configuration of the closely-defined beam, so that the system can be used to effectively match the radiated volume to the shape of the tumor volume.

The present invention may be implemented by mounting an X-ray tube, capable of generating a point source, mid-energy beam, or multiples of such X-ray tubes, on one or more suitable mechanical gantries, such that the X-ray tube (or X-ray tubes) can be adjustably directed toward the isocenter of the treatment volume, e.g., so that the X-ray tube (or X-ray tubes) can be schematically positioned on the inner surface of an imaginary sphere (or other curved geometry). By way of example but not limitation, a metallic or non-metallic C-arm may be provided, wherein the C-arm carries an X-ray source and an associated beam collimator that can move along the C-arm, while centered on the treatment volume, such that the X-ray source can direct its beam to the treatment volume using a plurality of different skin entry portals. The C-arm may be movably mounted on bearings so as to provide a wider range of X-ray tube positions, and hence a wider range of skin entry portals.

Although highly variable with X-ray tube design, filtration and energy, approximately 2 to 4 Gy per minute per source may be delivered to the treatment volume where the source is set 660 mm from the treatment volume and the treatment volume is located 10 cm inside the body. This level of radiation output would indicate a 25 minute treatment time with one X-ray tube source and a 10 to 15 minute treatment time with two X-ray tube sources, for delivering a 20 Gy treatment dose 10 cm inside the body. Of course, in accordance with the present invention, the 20 Gy treatment dose is delivered by using a plurality of skin entrance portals so that each skin entrance portal receives no more than 2 Gy at any one skin entrance portal. Two X-ray tube sources are generally preferred over more than two X-ray tube sources for a number of reasons, including less collision interference (between the X-ray tube sources) with only two trajectories. In accordance with the present invention, the distance between the X-ray tube source(s) and the target tissue is reduced to 660 mm, as compared to the traditional distance of 1.0 meter or 0.8 meter, in order to approximately double the amount of radiation delivered to the treatment volume per source, while still maintaining the beam resolution desired. The desired X-ray beam may be created by using a small focal spot source (e.g., about 1.0 mm) tailored with a collimator, e.g., a 1 mm MLC. The desired small focal point X-ray beam may be achieved by using a more acute X-ray anode angle, usable with the intended small fields, and thus a smaller focal spot projection, while keeping power levels high (e.g., 4-5 kW). Certain recent very high power rotating anode X-ray tube designs now used in CT can be adapted to this concept by engineering effort; at present a 25 kW steady state power level is possible which can reduce these example times by a factor of 5× or 10×.

Improvements in dielectric sciences and insulation has also raised the "reasonable" kVp level to the 600 kVp level.

The patient table, and thus the tumor location (which is indexed to the table by known stereotactic methods, and possibly checked by mounting imaging components on the same X-ray system), is adjusted in an X-Y-Z, micrometer motion relative to the mechanical gantry, and hence relative to the X-ray source(s) movably mounted to the mechanical gantry.

The present invention is intended to enable radiosurgical ablations with beams of approximately 50 mm or less (and preferably of about 15 mm) in a manner inherently much more precise than Linac or Gamma Knife designs, and at a lower cost. Radiation shielding for 350 kVp to 600 kVp beams is minimal compared to MeV devices, greatly lowering installed cost, while providing a better, more well-defined and more controllable bolus of radiation. From a cost-of-treatment perspective, 3 or 4 systems of the present invention can be installed for the cost of a single Linac system. Significantly, no radiation-protective "bunker" construction is required.

At the same time, in addition to providing radiotherapy, the mid-voltage, small area X-ray sources (and collimators) can be used to provide exquisite X-ray imaging of the patient anatomy. Note that Linac and Gamma Knife designs do not provide this opportunity. By way of example but not limitation, a flat plate X-ray imager (e.g., such as the Paxscan flat plate X-ray imager made by Varian) may be placed on the far side of the anatomy, such that the therapeutic X-ray source can be used with the X-ray imager to image the anatomy.

More particularly, the therapeutic X-ray source and the X-ray imager may be used to confirm accurate placement of the tumor (i.e., the treatment volume) at the isocenter of the therapeutic X-ray beam, e.g., by using a reduced intensity X-ray beam and, optionally, a contrast agent. The patient table may be adjusted as needed in order to precisely align the tumor (i.e., the treatment volume) with the isocenter of the X-ray beam. Once the tumor (i.e., the treatment volume) has been properly aligned with the isocenter of the X-ray beam, therapeutic X-ray radiation may then be precisely delivered to the tumor.

In addition, the X-ray imager (combined with a reduced intensity X-ray beam) may be used to verify that the actual MLC openings conform to the pre-planned MLC openings (i.e., to confirm that the MLC leaflets are operating properly), so as to ensure that the correct pre-planned treatment dose is delivered to the treatment volume.

And the X-ray detector may also be used to ensure that the correct radiation dose is delivered to the treatment volume during therapy, i.e., by monitoring the radiation received at the X-ray detector during radiation therapy.

In one preferred form of the invention, there is provided a radiotherapy system comprising an X-ray tube operating at 100 to 800 kVp for providing X-ray beams of 50 mm diameter or less (and preferably approximately 30 mm or less) and configured to move the entrance beam footprint on the body during irradiation to any arbitrary sequential position set that has been predetermined to limit the intervening tissue dose rate at any one location to a safe level, such that the sum of the skin area traversed during treatment is 20 to 100 times the beam area.

In another preferred form of the invention, there is provided a radiotherapy system, the system comprising:
a gantry;
at least one X-ray tube movably mounted to the gantry, wherein the at least one X-ray tube operates at 100 kVp to 800 kVp and has a beam origin of 1.5 mm or less;
a collimator associated with the at least one X-ray tube for collimating the X-ray beam from the X-ray tube to 50 mm or less;
wherein the gantry and the at least one X-ray tube are configured so that (i) the X-ray beam from the at least one X-ray tube is always centered on a treatment volume, and (ii) the skin entrance portal of the X-ray beam may be moved on the body during therapy so that the total area of the skin entrance portals is 20 to 100 times the X-ray beam area.

In another preferred form of the invention, there is provided a method for providing radiotherapy to a treatment volume, the method comprising:
providing a radiotherapy system, the system comprising:
a gantry;
at least one X-ray tube movably mounted to the gantry, wherein the at least one X-ray tube operates at 100 kVp to 800 kVp and has a beam origin of 1.5 mm or less; and
a collimator associated with the at least one X-ray tube for collimating the X-ray beam from the X-ray tube to 50 mm or less;
wherein the gantry and the at least one X-ray tube are configured so that the X-ray beam from the at least one X-ray tube is always centered on a treatment volume; and
radiating the treatment volume using the X-ray beam, with the X-ray tube being moved so that the skin entrance portal of the X-ray beam is moved on the body during therapy so that the total area of the skin entrance portals is 20 to 100 times the X-ray beam area.

In another preferred form of the invention, there is provided an X-ray source configured to serve the dual purpose of radiation therapy and imaging.

In another preferred form of the invention, there is provided a two dimensional imaging detector configured to serve the dual purpose of imaging and dose measurement.

In another preferred form of the invention, there is provided a radiotherapy system comprising X-ray source configured to serve the dual purpose of radiation therapy and imaging and a two dimensional imaging detector configured to serve the dual purpose of imaging and dose measurement, the X-ray source and the two dimensional imaging detector being arranged on two opposite sides of a rotatable arcuate structure, with the patient under treatment at the center of the rotatable arcuate structure, around which the X-ray source and the two dimensional imaging detector are scanned.

In another preferred form of the invention, there is provided a radiotherapy system, the system comprising:
a gantry;
at least one X-ray tube movably mounted to the gantry, wherein the at least one X-ray tube operates at 100 kVp to 800 kVp and has a beam origin of 1.5 mm or less;
a collimator associated with the at least one X-ray tube for collimating the X-ray beam from the X-ray tube to 50 mm or less;
wherein the gantry and the at least one X-ray tube are configured so that (i) the X-ray beam from the at least one X-ray tube is always centered on a treatment volume, and (ii) the skin entrance portal of the X-ray beam may be moved on the body during therapy so that the total area of the skin entrance portals is 20 to 100 times the X-ray beam area; and
at least one imaging detector movably mounted to the gantry, the at least one imaging detector being disposed diametrically opposite to the at least one X-ray tube;
wherein the at least one X-ray tube and the at least one imaging detector are configured to operate in an imaging mode to determine the disposition of the treatment volume relative to the gantry;
and further wherein the at least one X-ray tube is configured to operate in a radiation therapy mode to deliver an X-ray beam to the treatment volume.

In another preferred form of the invention, there is provided a method for operating a radiotherapy system, the method comprising:
providing a radiotherapy system, the system comprising:
a gantry;
at least one X-ray tube movably mounted to the gantry, wherein the at least one X-ray tube operates at 100 kVp to 800 kVp and has a beam origin of 1.5 mm or less;
a collimator associated with the at least one X-ray tube for collimating the X-ray beam from the X-ray tube to 50 mm or less;
wherein the gantry and the at least one X-ray tube are configured so that (i) the X-ray beam from the at least one X-ray tube is always centered on a treatment volume, and (ii) the skin entrance portal of the X-ray beam may be moved on the body during therapy so that the total area of the skin entrance portals is 20 to 100 times the X-ray beam area; and
at least one imaging detector movably mounted to the gantry, the at least one imaging detector being disposed diametrically opposite to the at least one X-ray tube;
wherein the at least one X-ray tube and the at least one imaging detector are configured to operate in an imaging mode to determine the disposition of the treatment volume relative to the gantry;

and further wherein the at least one X-ray tube is configured to operate in a radiation therapy mode to deliver an X-ray beam to the treatment volume;

operating the at least one X-ray tube and the at least one imaging detector in the imaging mode to determine the disposition of the treatment volume relative to the gantry; and operating the at least one X-ray tube in the radiation therapy mode to deliver an X-ray beam to the treatment volume.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 20 and 21 are schematic views showing another form of radiotherapy system formed in accordance with the present invention, wherein the radiotherapy system is configured to provide image guided radiation therapy.

DETAILED DESCRIPTION OF THE PREFERRED EMBODIMENTS

Figure 1:
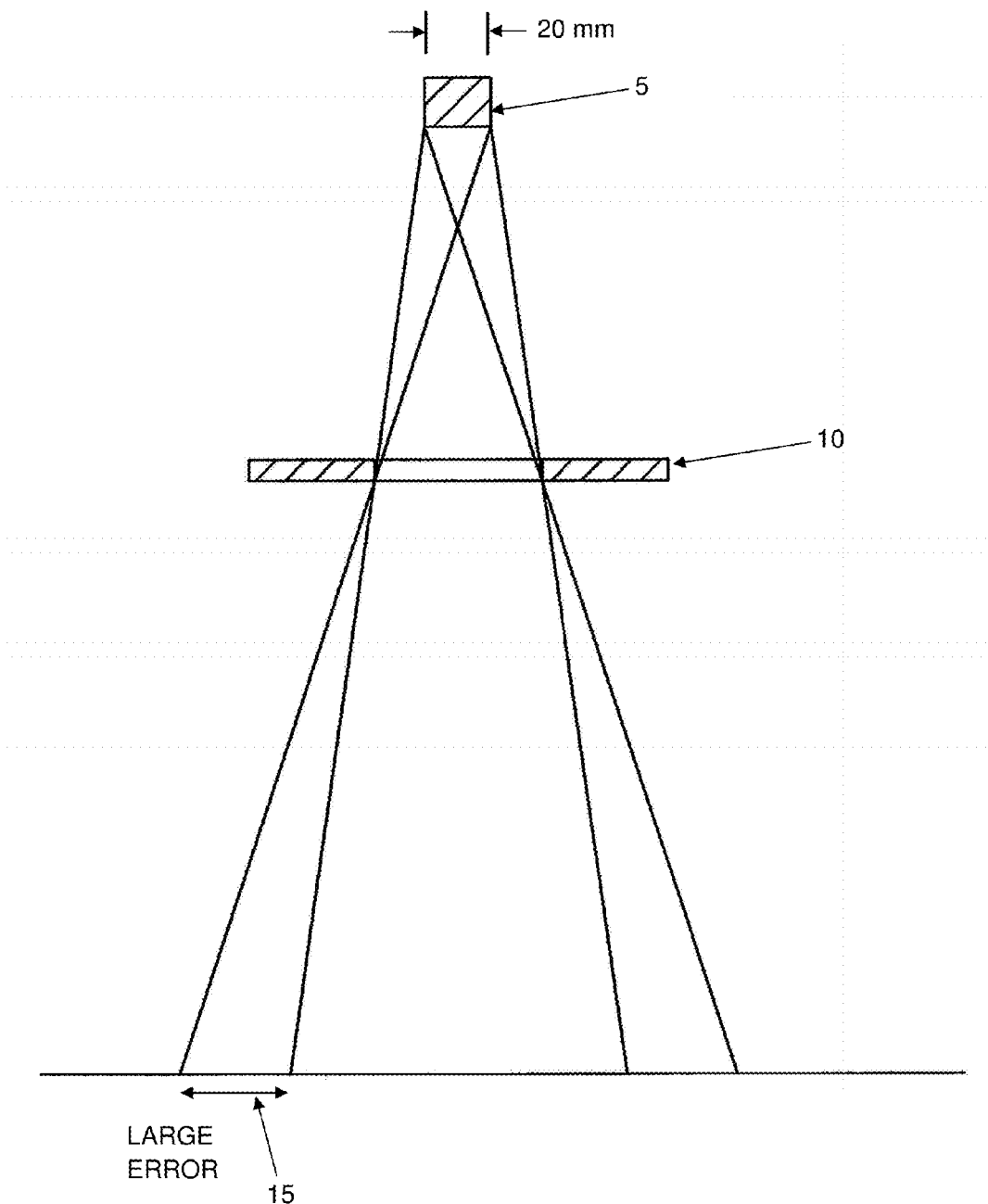
FIG. 1 is a schematic view showing a typically large cobalt source of about 20 mm size, as is commonly used in Gamma Knife systems—as can be seen from the figure, it is not possible to collimate such a large source to a sharp beam edge.
Figure 2:
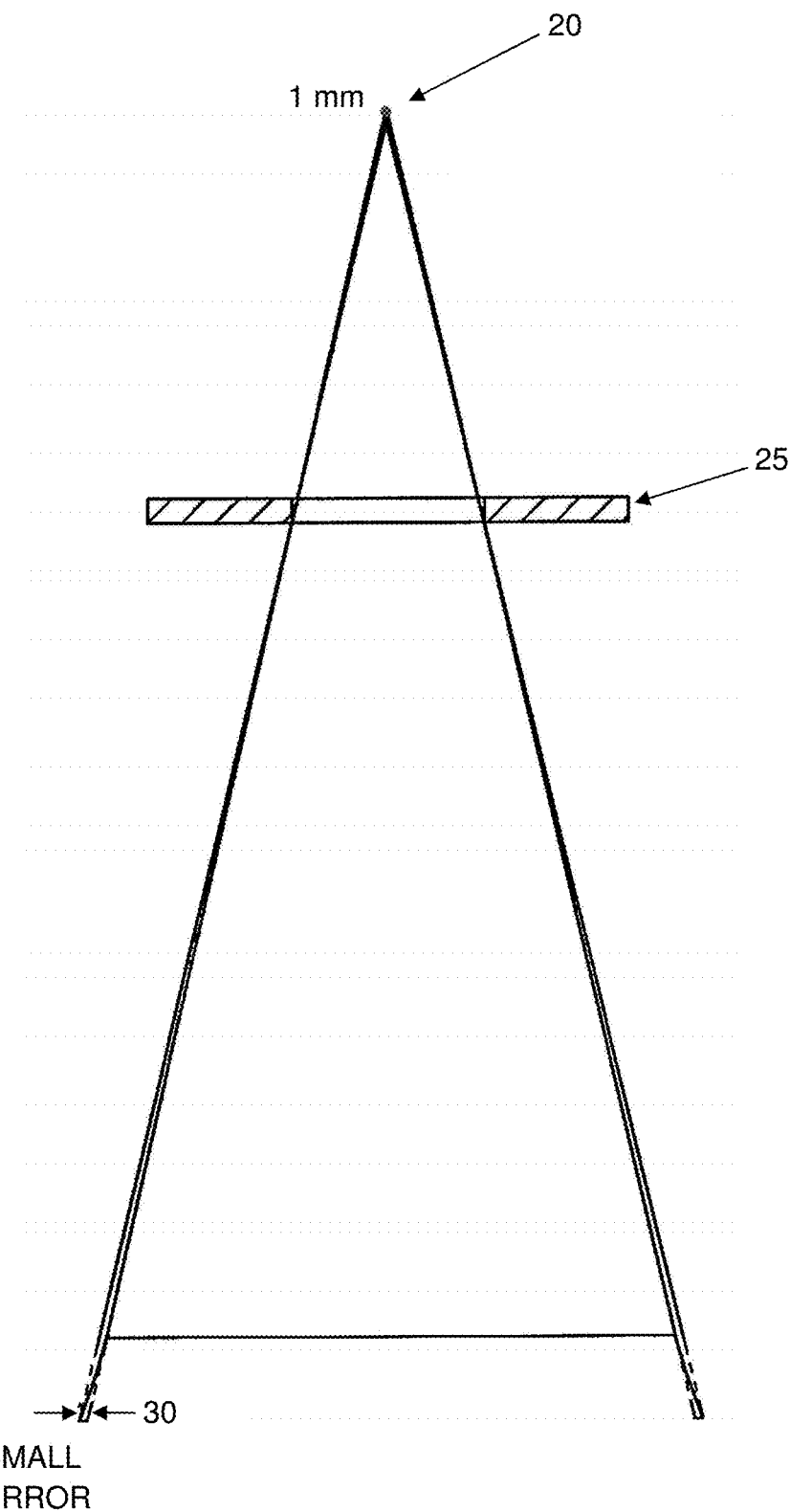
FIG. 2 is a schematic view showing the sharp beam edge which can be provided by a 1 mm X-ray source (or focal spot)
Figure 3:
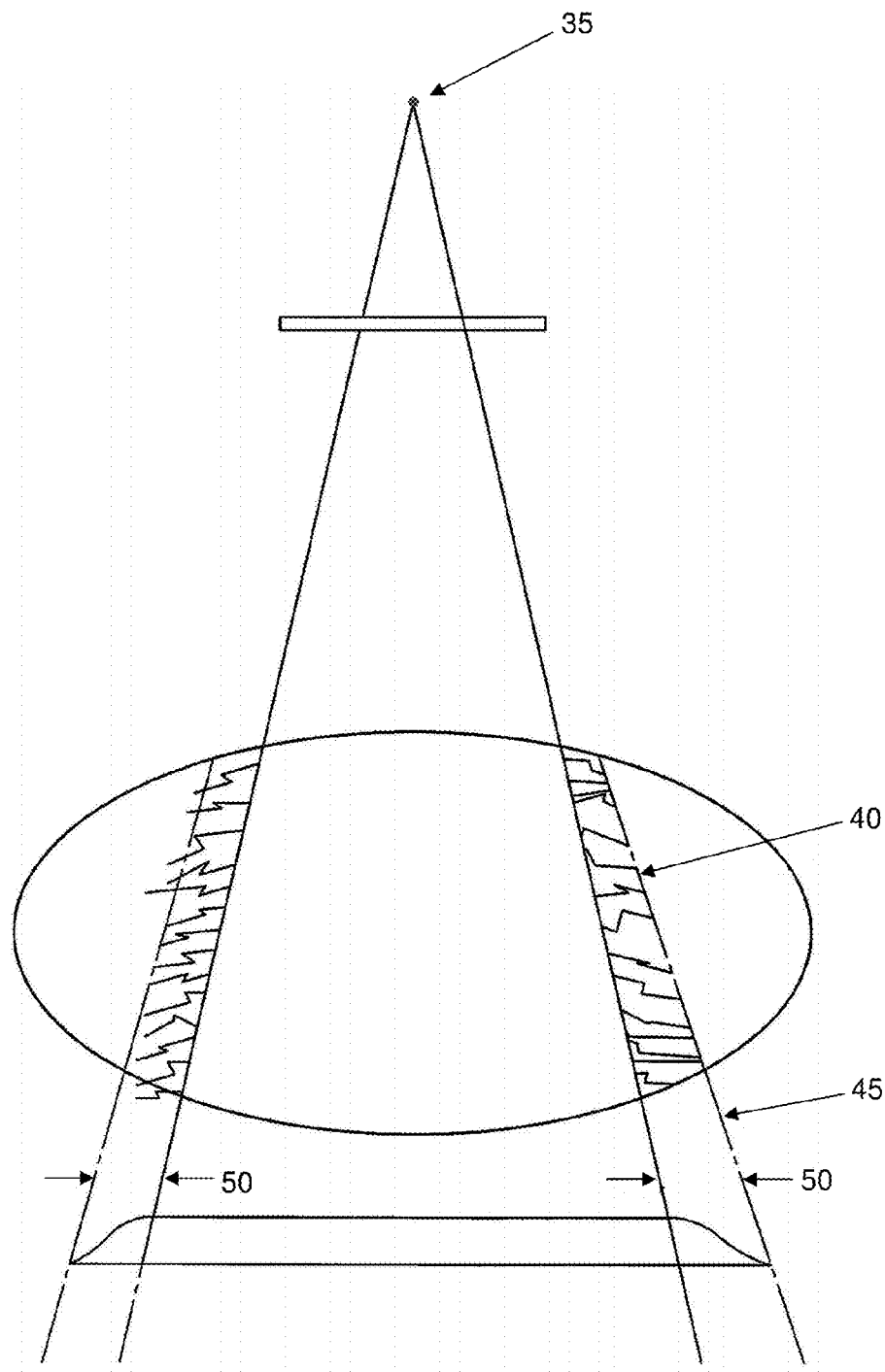
FIG. 3 is a schematic view showing a typical 6 MeV Linac beam, with secondary radiation generated by scatter interactions within the body extending out approximately 10 mm beyond the normal boundary of the geometric beam—thus, even if the 6 MeV Linac beam has excellent collimation, beam scattering within tissue eliminates any possibility of a sharp beam edge.
Figure 4:
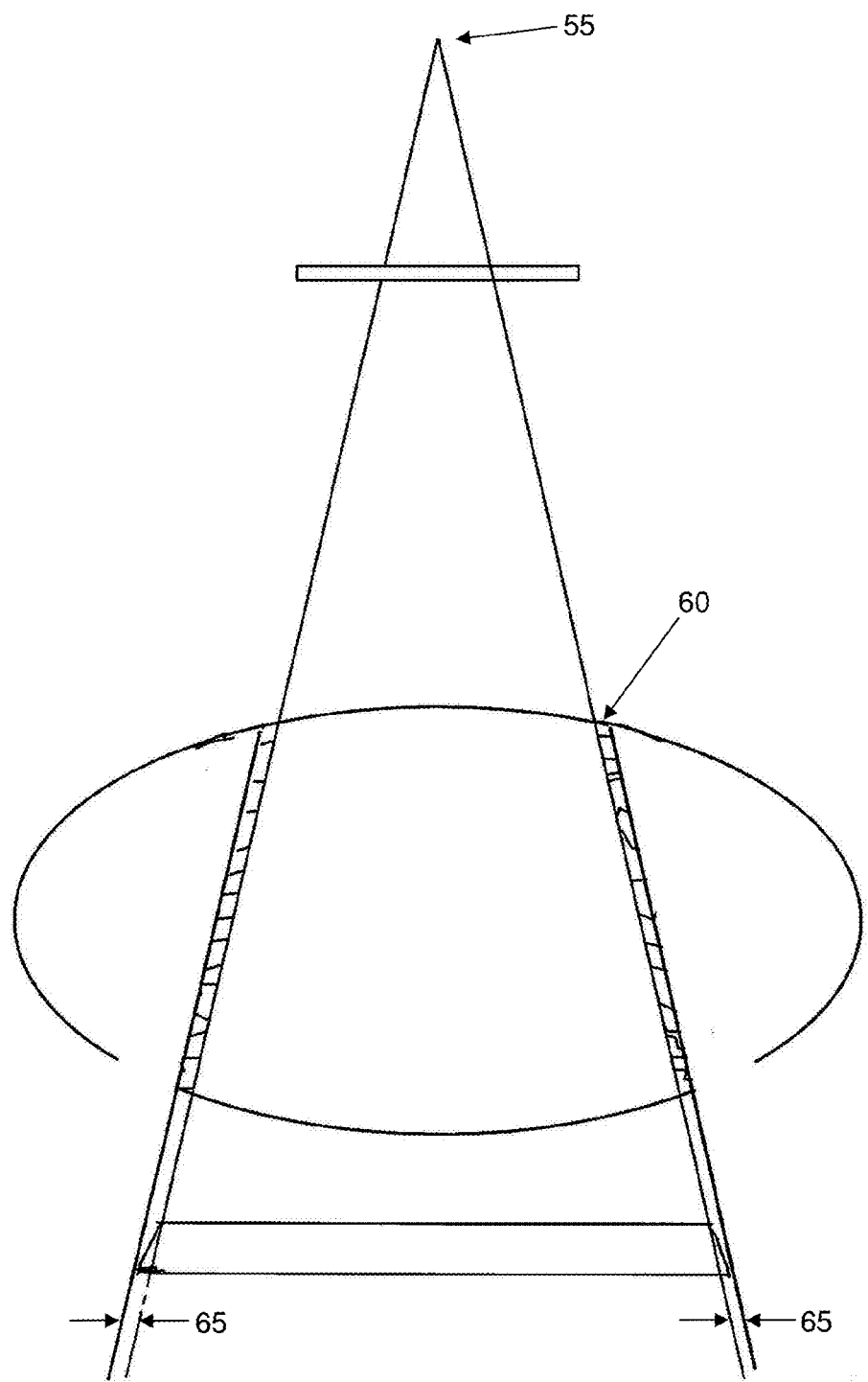
FIG. 4 is a schematic view showing how a 1.0 mm X-ray source, operating at 100-800 kVp, generates only short-range Compton scatter, and hence generates a sub-1 mm to about 1 mm error beyond the geometric beam.
Figure 5:
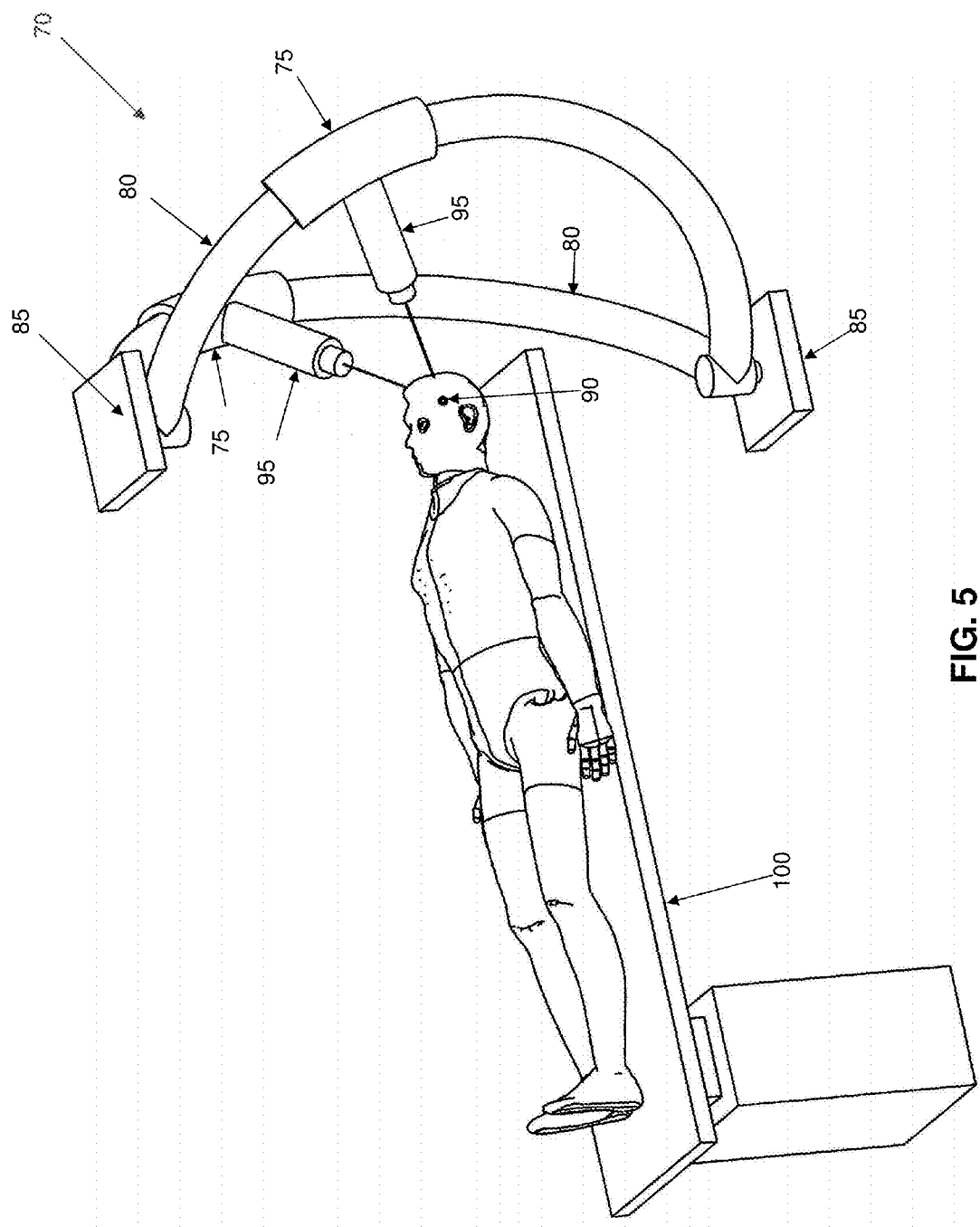
FIG. 5 is a schematic view showing a radiotherapy system which comprises one preferred form of the present invention, wherein the radiotherapy system comprises a plurality of C-arms mounted to a vertical axis bearing, wherein each of the plurality of C-arms carries an X-ray source (and associated collimator) that can move along the arc of the C-arm while centered to a treatment volume.

Looking now at FIG. 5, in accordance with the present invention, there is provided a radiotherapy system 70 which comprises two X-ray tubes 75 which are mounted to two C-arms 80 which are pivoted through generally vertical axis bearings with common centers 85, aligned with the spherical isocenter 90. X-ray tubes 75 are mid-voltage devices, operating at 100 kVp to 800 kVp, and have a small point source (e.g., 0.6 mm-3 mm). The two X-ray tubes 75 will always point, during a treatment, at isocenter 90. The X-ray beams of X-ray tube 75 are collimated with collimators 95 so as to produce a small diameter (e.g., 50 mm or less, and preferably of about 15 mm), well-defined (e.g., with little collimation error) beam, such that approximately 50 (or less) skin entrance portals may be used to direct well-defined beams of radiation at the treatment volume. Preferably collimators 95 are multi-leaf collimators (MLC), which need not operate symmetrically about the beam axis, such that collimators 95 can shift the net beam irradiated field to one side or the other of the X-ray tube central ray line.

The rotation about the vertical axis 85-85 of C-arms 80 are driven by independent motors associated with the bearings 85 to precisely position the C-arms 80 rotationally around axis or center line 85-85.

X-ray tubes 80 and collimators 95 can "climb" up and down C-arms 80 under precise control of motors, using computer feedback methods.

Multi-leaf collimators 95 may open and close as they travel, to track a known projection or shape of the tumor as viewed from their instantaneous perspective. This data is derived from 3D CT images in known ways, and this process is allowed for by design, by making multi-leaf collimators 95 fast enough to follow this.

The axis 85-85 may be tilted, or the patient head tilted, to best access the treatment zone.

The volume to be radiated is positioned to isocenter 90 by precise X-Y-Z motions of the table 100. Table 100 may or may not move during treatment, under control of treatment planning software. X-ray tubes 75 are generally operated in this device at 100 kVp to 800 kVp, and preferably at 300 kVp to 500 kVp. X-ray tubes 75 preferably have a shallow anode angle of approximately 8 to 16 degrees to address high loading of a nominal 1 mm source size. X-ray tubes 75 may be rotating anode X-ray tubes or stationary anode X-ray tubes.

Figure 6:
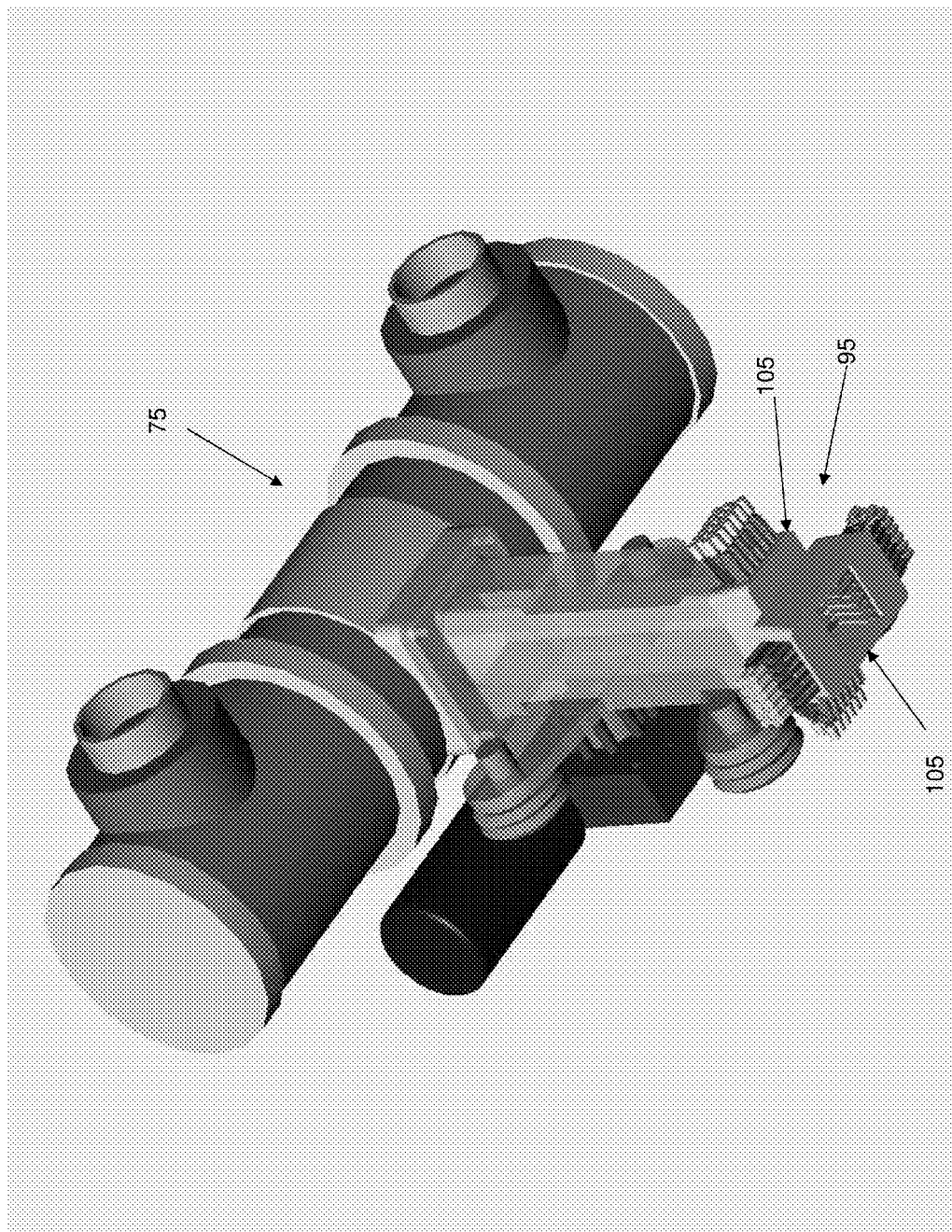
FIGS. 6-8 are schematic views showing construction details of an X-ray source and associated collimator of the sort which may be utilized in the radiotherapy system shown in FIG. 5.
Figure 7:
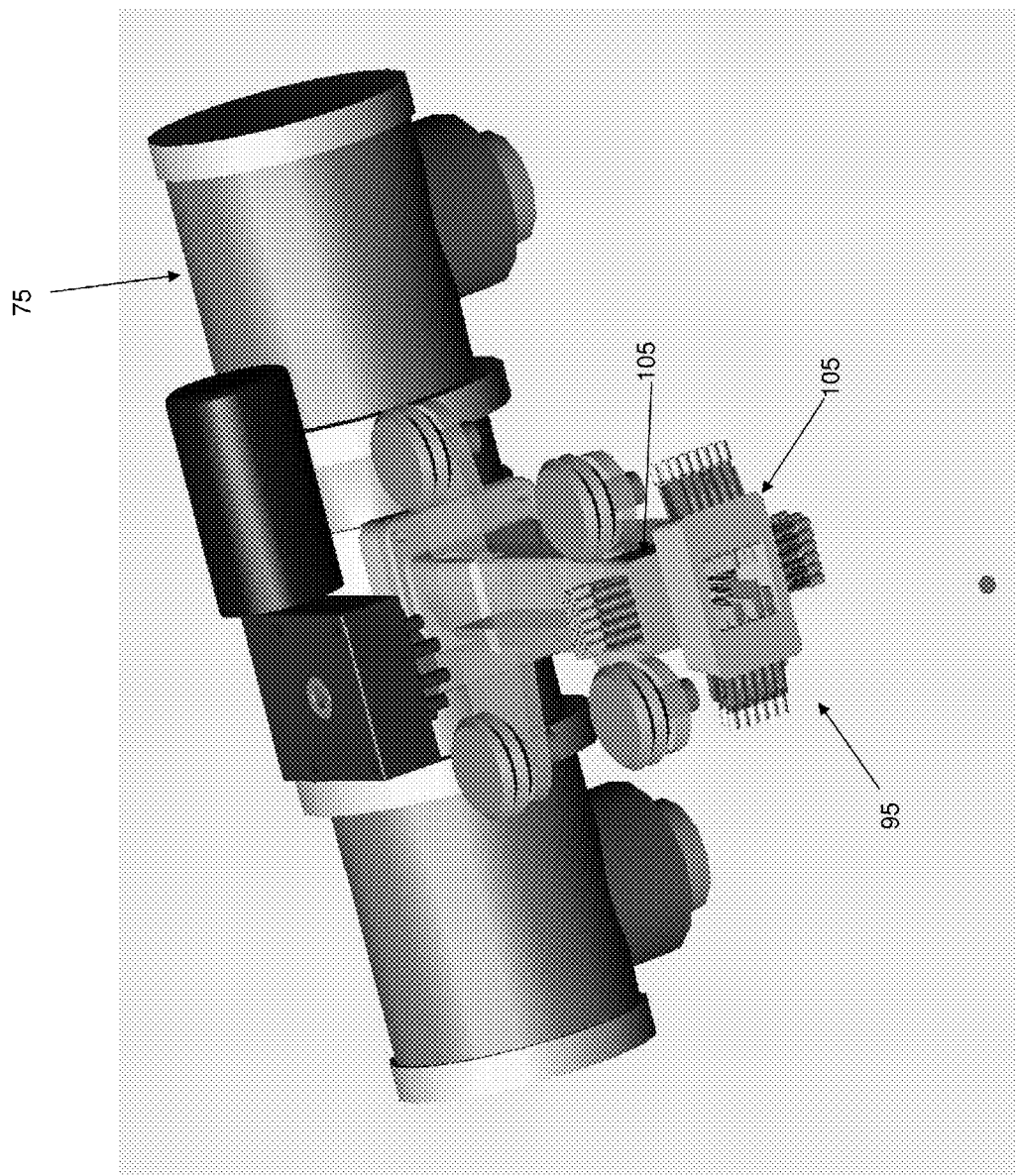
Figure 8:
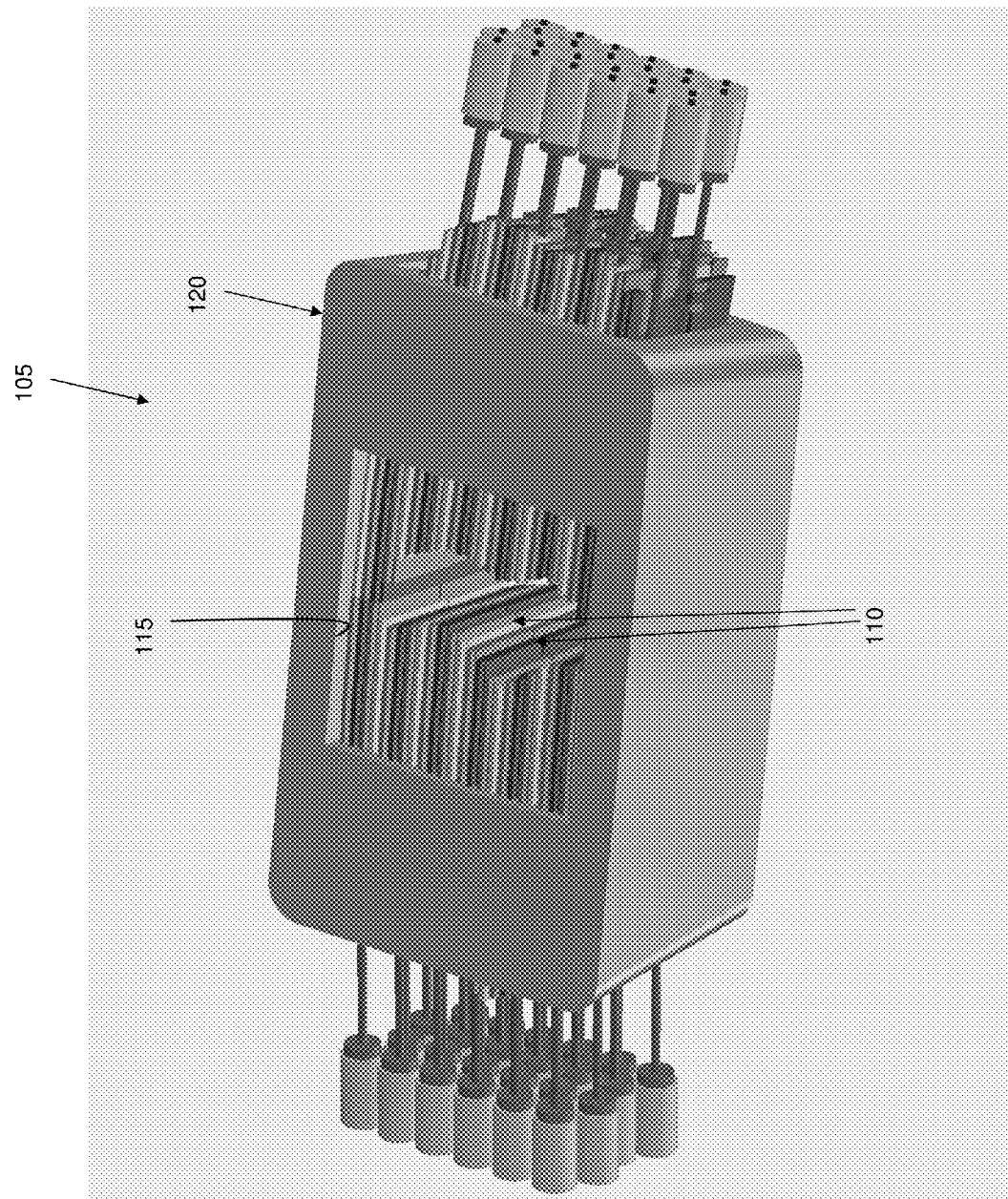

Multi-leaf collimators 95 are preferably composed of about thirty-two 1.5 mm leafs on each of the four sides. Each leaf is about 15 mm tall, made of tungsten, and each has its own drive nut screw, motor and feedback of position, so 128 motors are used per collimator. More or fewer motors can be used depending on the maximum beam cross-section desired, and the leaf dimension. By way of example but not limitation, and looking now at FIGS. 6 and 7, there is shown an exemplary collimator 95 mounted to an X-ray tube 75. In one preferred form of the invention, collimator 95 comprises a pair of collimator assemblies 105, wherein each of the collimator assemblies 105 comprises a plurality of leafs 110 which may be adjustably positioned within the opening 115 of a housing 120. Preferably collimator assemblies 105 are set in series, and perpendicular to one another.

X-ray tubes 75 are preferably operated at about 4.5 to 5.0 kW on constant potential DC power supplies, and if of special known design, up to 5 times that. They are oil-cooled by circulating pumps. They have filters specific to the HVL Cu desired, generally between 1.2 and 3.0 mm HVL, and may be multi-layer filters.

For use in neuroradiosurgery, precision table 100 enters the arcs of C-arms 80 horizontally to position the head and tumor to within 1 mm of isocenter 90. Various head frames and frameless approaches can be used to immobilize the head and register it into the overall system coordinate system, which should be accurate to about 1 mm.

Thus it will be seen that, in accordance with the present invention, there is provided a radiotherapy system 70 which generally comprises a gantry or gimbal, etc. (which generally comprises at least one C-arm 80) upon which at least one X-ray source (which preferably comprises at least one X-ray tube 75 and associated collimator 95) is movably mounted. The geometry of the gantry (or gimbal) and the X-ray source are such that the X-ray source is always focused at an isocenter 90 regardless of the position of the X-ray source along the gantry (or gimbal); however, inasmuch as the X-ray source is movable along the gantry (or gimbal), the system allows the radiation beam emanating from the X-ray source to be directed at isocenter 90 from a variety of angles, whereby to provide a large number of different skin entrance portals. Preferably the gantry (or gimbal) is movable relative to the isocenter (e.g., each C-arm 80 is pivotable about an axis) so as to increase the range of positions from which the X-ray source may be directed at isocenter 90, and hence further increases the range of different skin entrance portals. In accordance with the present invention, each of the X-ray sources comprises a mid-voltage X-ray source (e.g., 100 kVp to 800 kVp) having a small beam origin (e.g., about 1 mm), such that when it is appropriately collimated by collimator 95 into a small diameter beam (e.g., 50 mm or less, and preferably of about 15 mm), provides a well-defined beam which is subject to minimal scattering within the tissue, whereby to provide a tightly constrained X-ray beam to the anatomy. In accordance with the present invention, there is also provided a motorized table 100 upon which the patient may be positioned, such that by precise movement of motorized table 100 relative to the gantry (or gimbal), the target tissue may be positioned at isocenter 90. As a result of the foregoing construction, the narrow, well-defined, mid-voltage X-ray beams may be directed at the isocenter from a substantial number of different positions (e.g., 50 or less), so as to deliver a therapeutic radiation dose to the isocenter while maintaining the radiation dose at each skin entrance portal below a harmful level.

Figure 9:
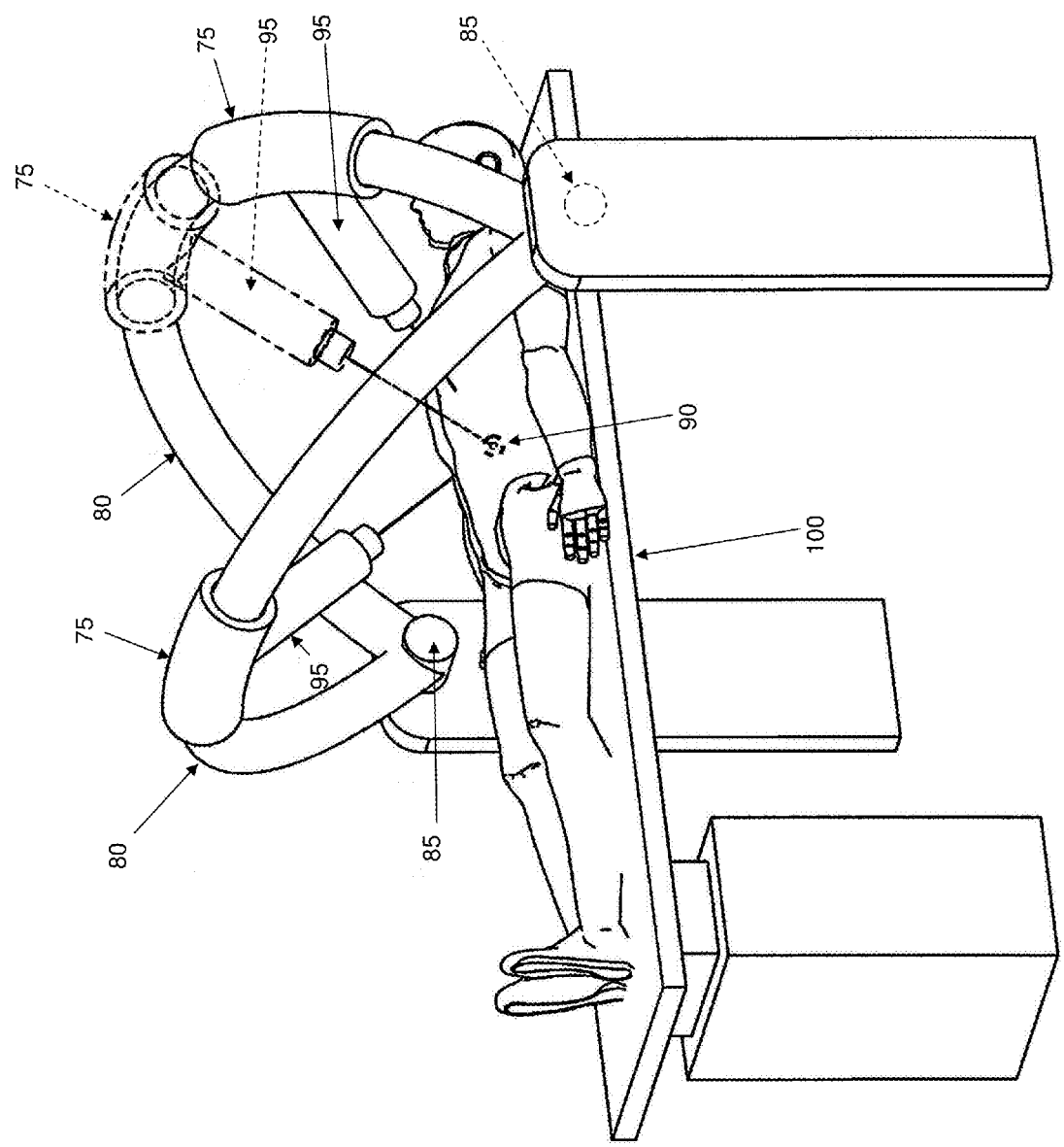
FIG. 9 is a schematic view showing another form of radiotherapy system formed in accordance with the present invention, wherein the radiotherapy system shown in FIG. 9 is generally similar to the radiotherapy system shown in FIG. 5 except that the C-arms are mounted to a horizontal axis bearing.

In FIG. 5, C-arms 80 are shown as pivoting through generally vertical axis bearings with common centers 85. However, as seen in FIG. 9, C-arms 80 may alternatively be configured so as to pivot through generally horizontal axis bearings with common centers 85. This configuration allows placement of X-ray tubes 75 along the long axis of the patient.

It will be appreciated by those skilled in the art that many other mechanical arrangements (e.g., robotic arms, hemispherical tracks, spirals in a plane, etc.) can be used to position the 100 kVp to 800 kVp X-ray tubes relative to the patient. The multi-arc systems shown in FIGS. 5-9 show just some of the possible embodiments of the present invention.

Figure 10:
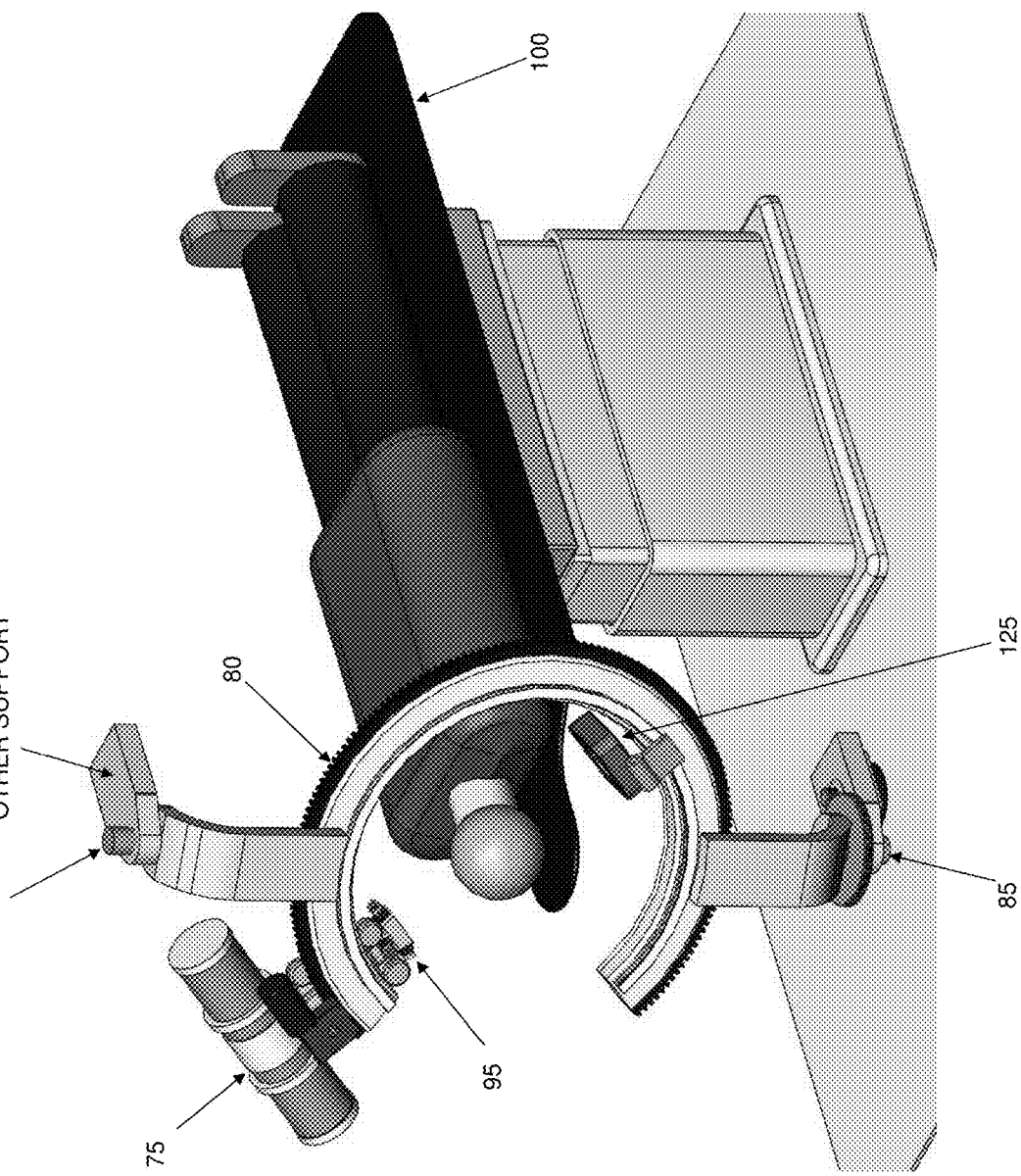
FIGS. 10 and 11 are schematic views showing another form of radiotherapy system formed in accordance with the present invention, wherein the radiotherapy system comprises an imaging device which allows imaging with the same X-ray tube used for providing radiotherapy.
Figure 11:
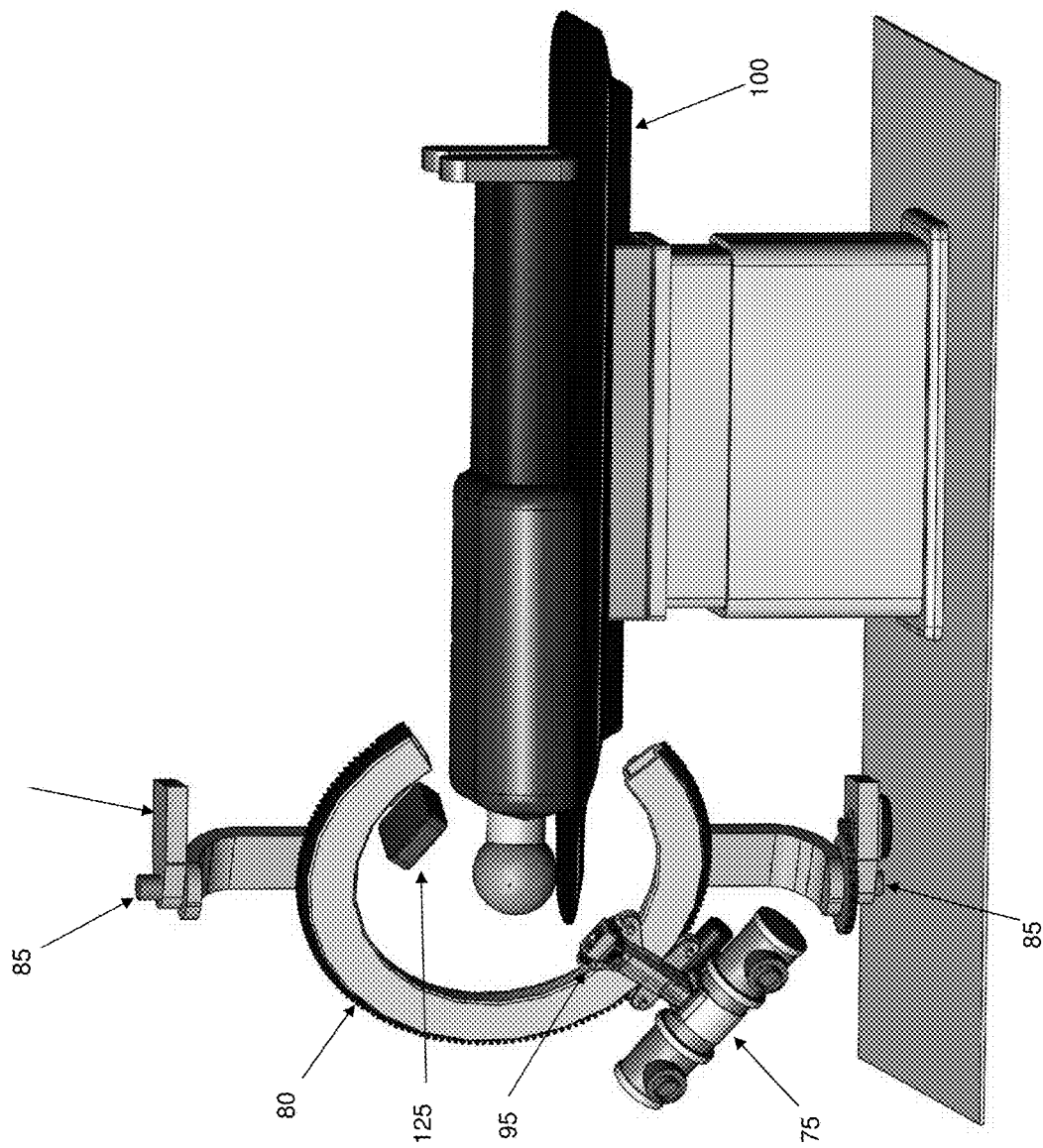

Looking next at FIGS. 10 and 11, imaging devices 125 (e.g., X-ray sensitive flat panels such as the Varian Paxscan 4030 of Varian Medical Systems, Salt Lake City, Utah) can be placed on the exit side of the beam trajectory by other known mechanical means, whereby to enable fluoro or cone beam CT, or projection imaging, even during treatment. In one preferred form of the present invention, the imaging plate is approximately 15 cm×approximately 30 cm. The imaging plate may incorporate a movable protective cover or shield so as to protect the imaging plate during long treatments, and/or the energy may be reduced during imaging.

Figure 12:
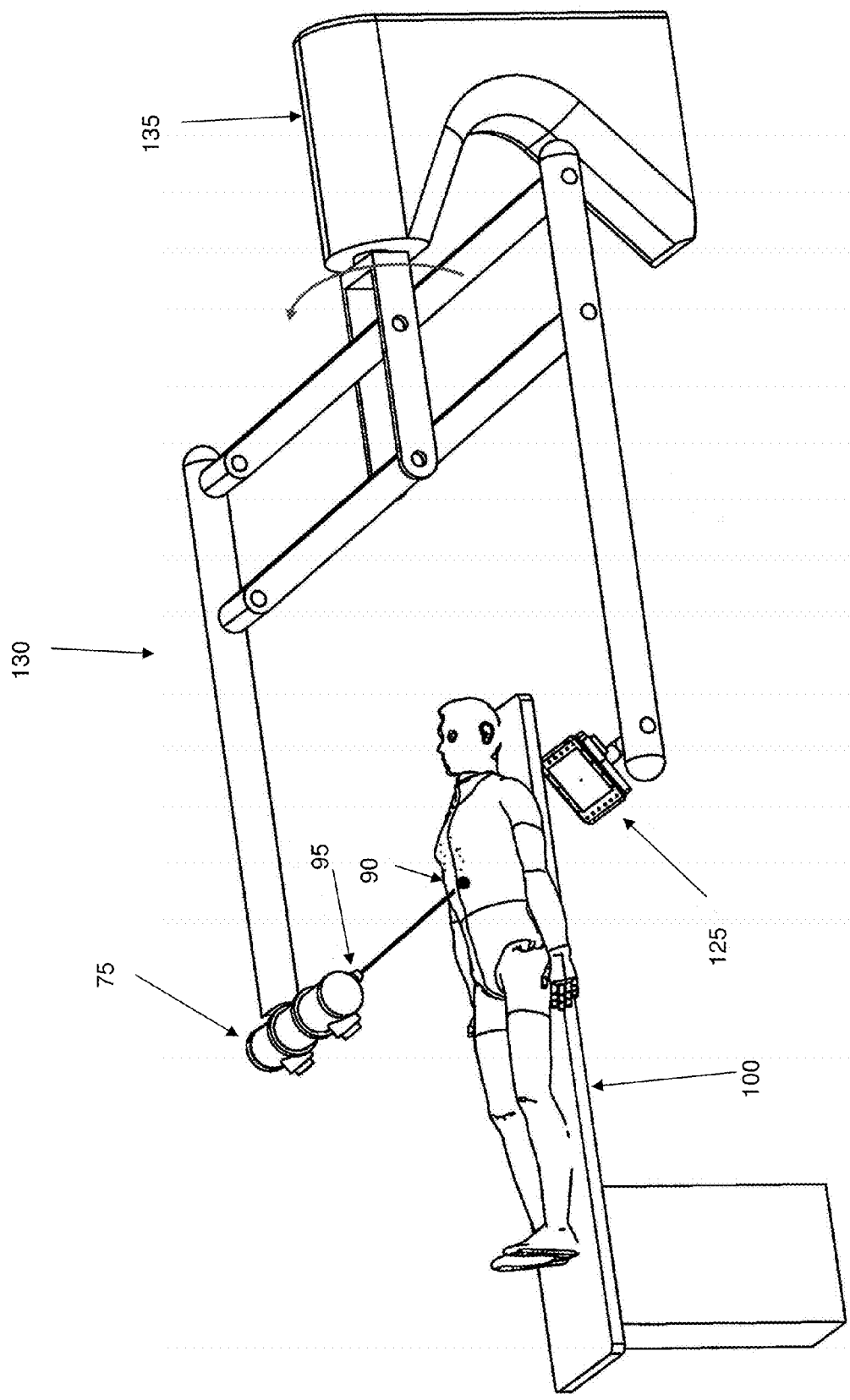
FIG. 12 is a schematic view showing another form of radiotherapy system formed in accordance with the present invention, wherein the radiotherapy system comprises an imaging device which allows imaging with the same X-ray tube used for providing radiotherapy, and further wherein the radiotherapy system comprises a gantry in the form of a rotatable parallelogram linkage that allows variable positioning of the X-ray source and imaging device relative to the isocenter.

FIG. 12 shows a parallelogram linkage 130 which is rotatably mounted to a support stand 135 and acts as the gantry for movably supporting X-ray tube 75 (and its associated collimator 95) and imaging device 125 relative to isocenter 90. If desired, parallelogram linkage 130 may be of the sort described and illustrated in U.S. Pat. No. 3,892,967, issued Jul. 1, 1975 to John K. Grady et al. for APPARATUS FOR RADIOLOGICAL EXAMINATION OF A SUBJECT THROUGH A SOLID ANGLE, which patent is hereby incorporated herein by reference.

Figure 13:
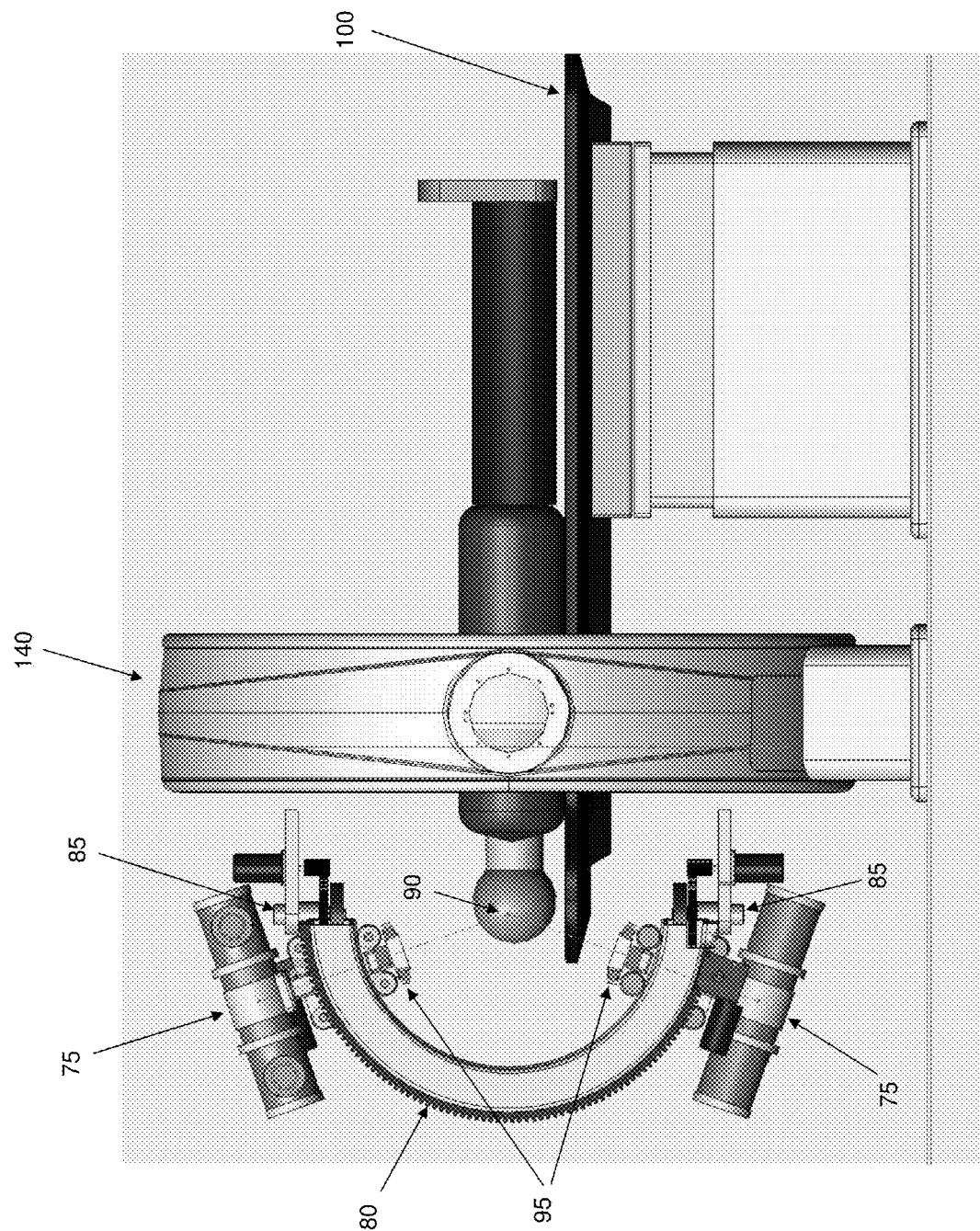
FIGS. 13 and 14 are schematic views showing another form of radiotherapy system formed in accordance with the present invention, wherein the radiotherapy system is provided in conjunction with a CT machine, and further wherein the radiotherapy system comprises a single C-arm movably carrying two X-ray sources thereon.
Figure 14:
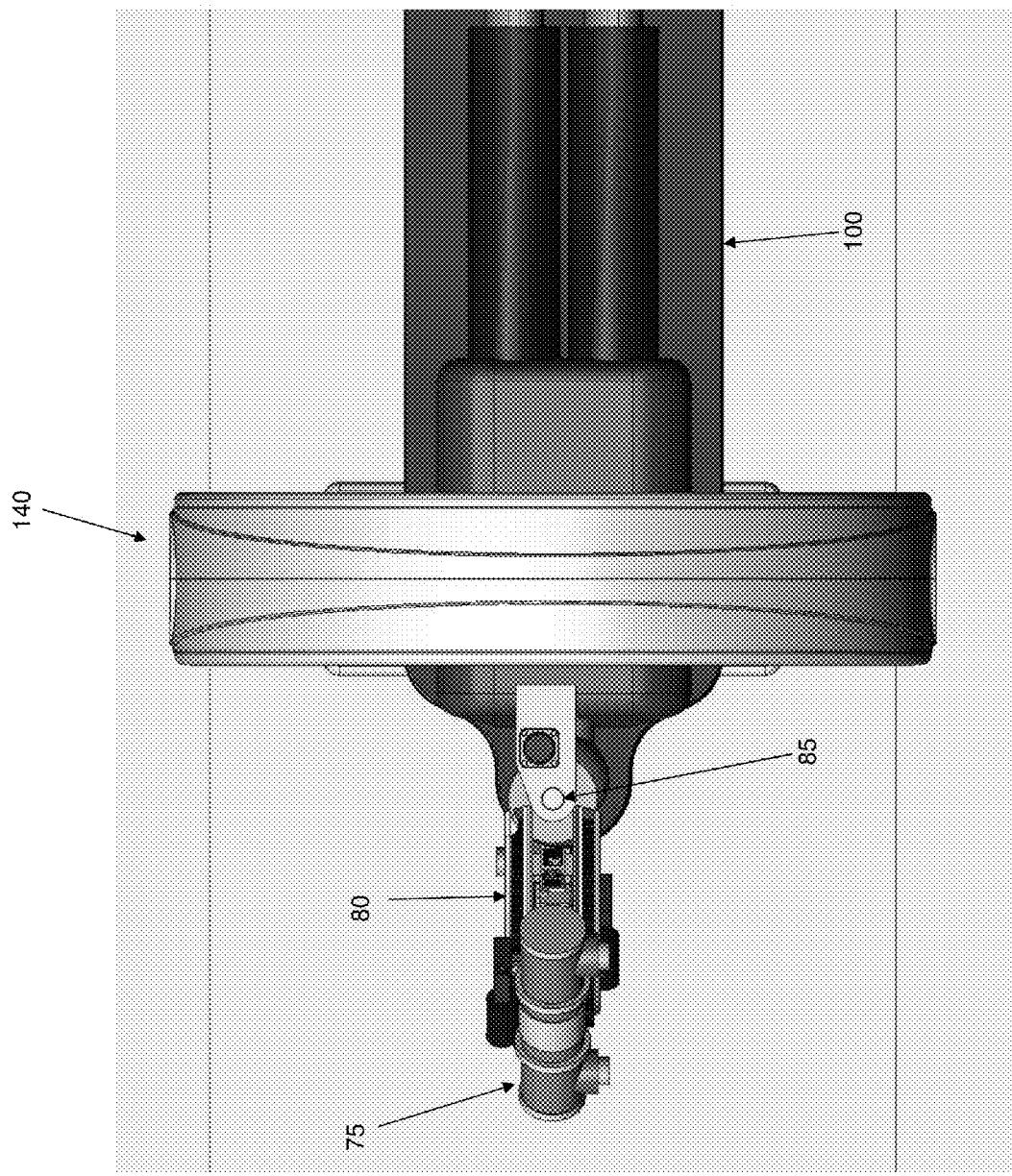
Figure 15:
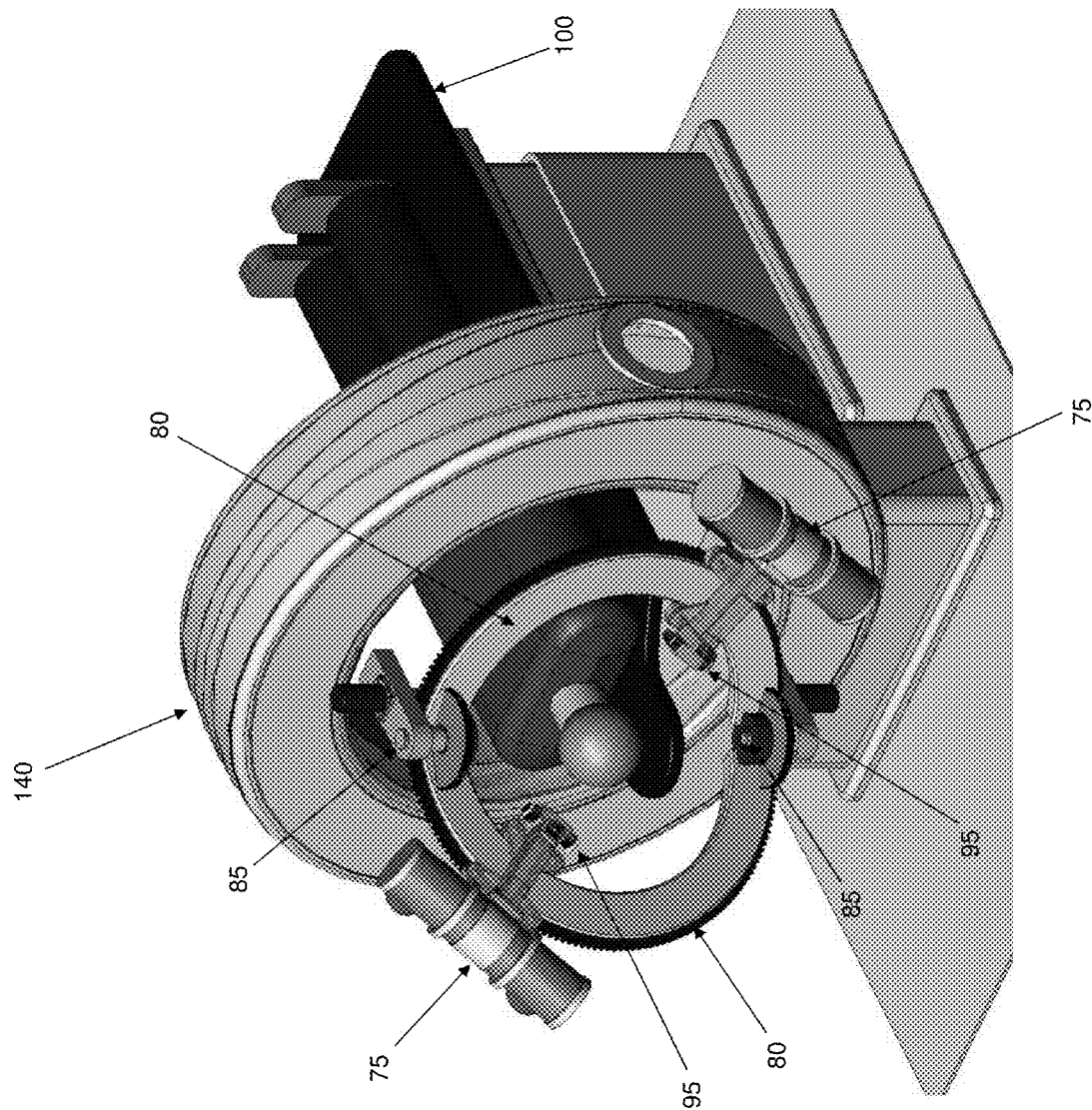
FIGS. 15-18 are schematic views showing another form of radiotherapy system formed in accordance with the present invention, wherein the apparatus is generally similar to the apparatus shown in FIGS. 13 and 14 except that the radiotherapy system comprises a two C-arms each movably carrying one X-ray source thereon.
Figure 16:
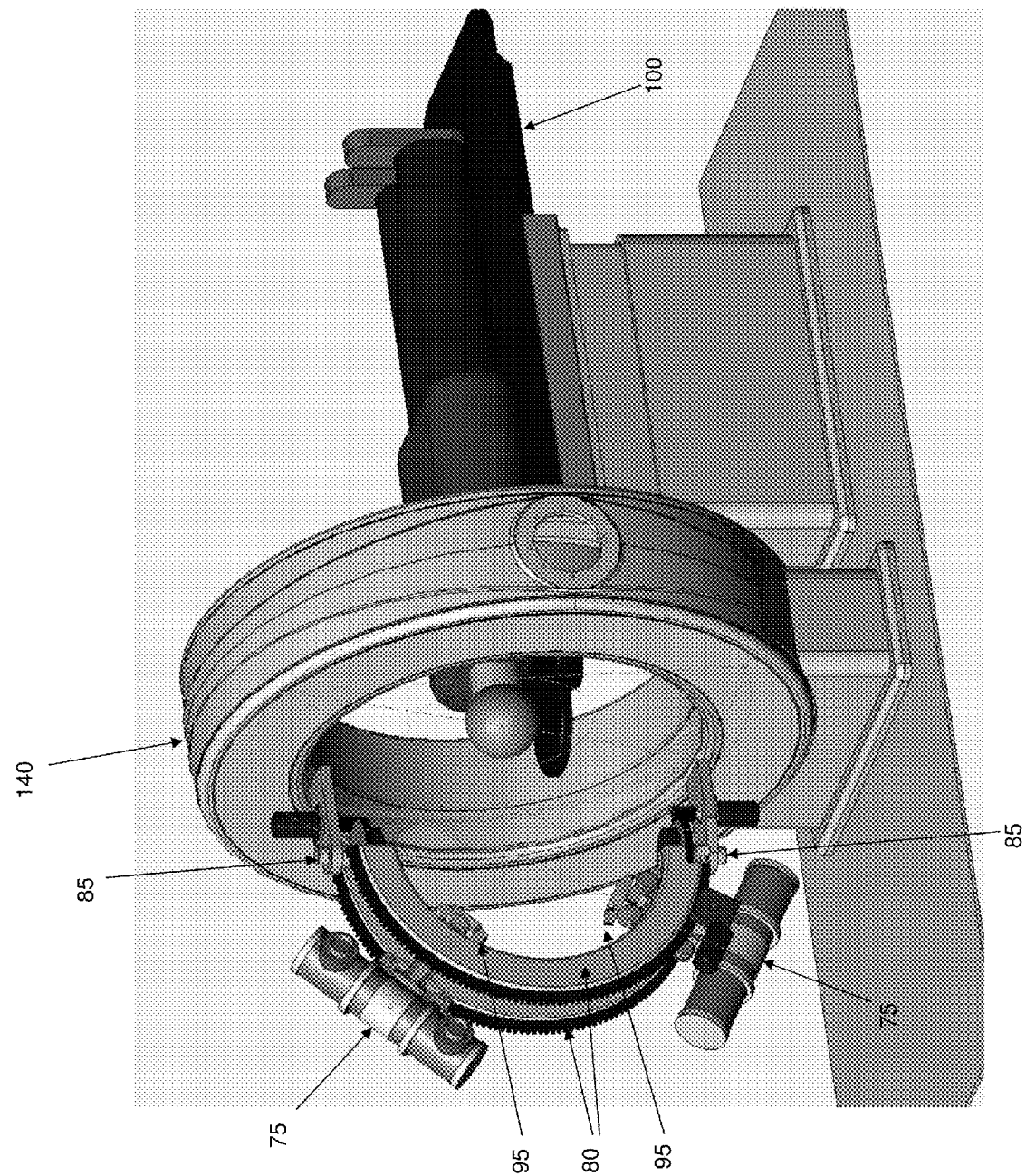
Figure 17:
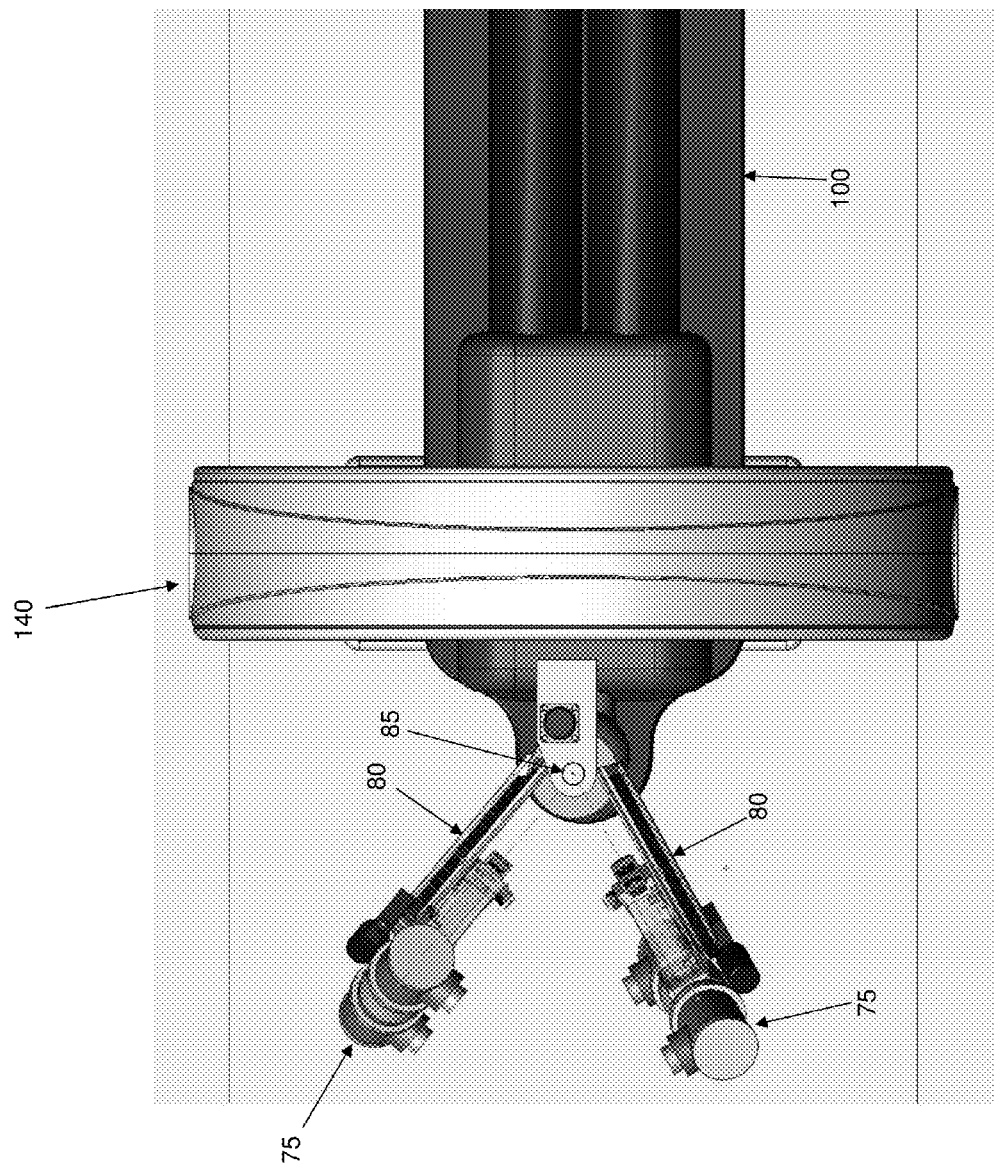
Figure 18:
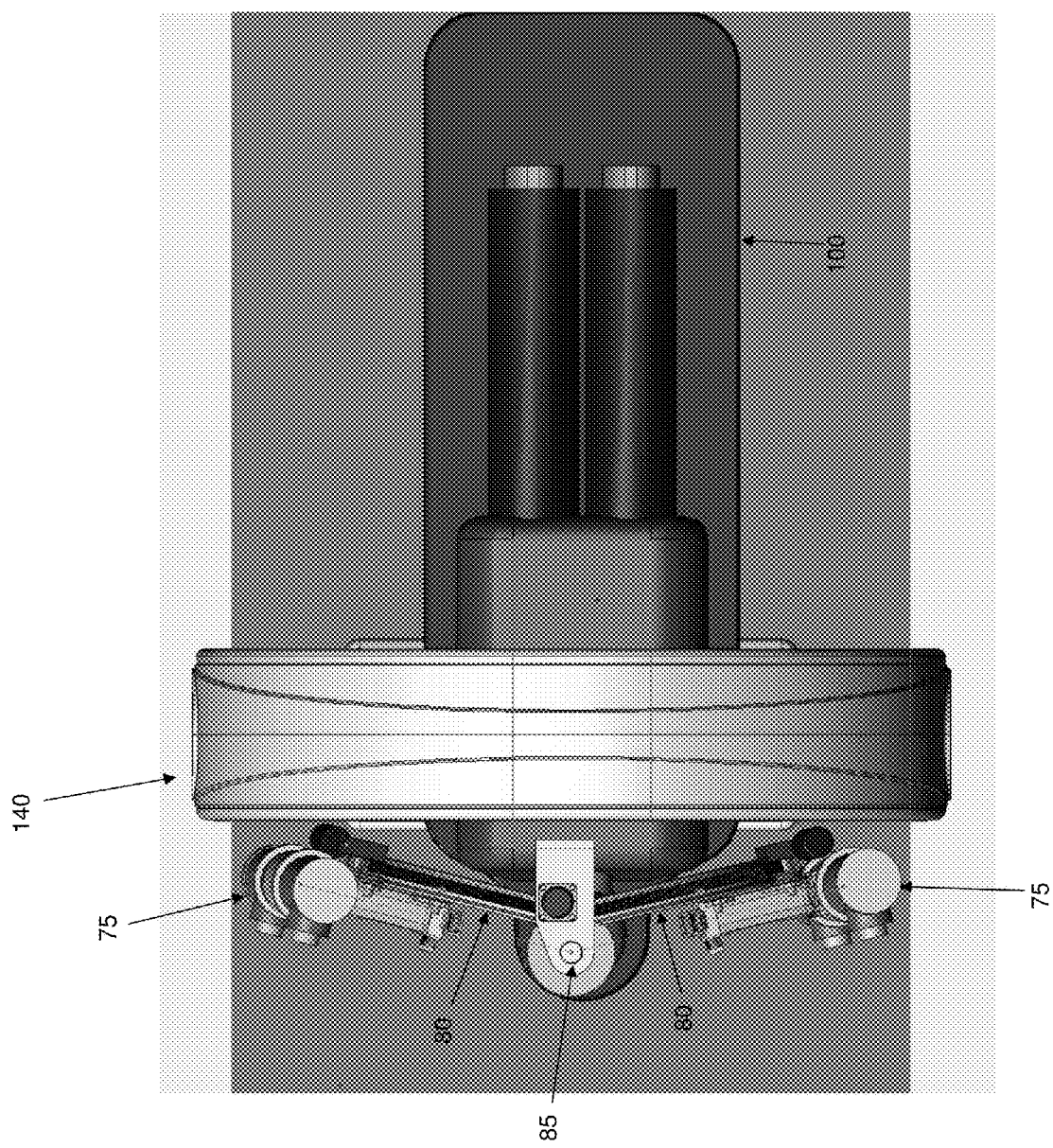

Looking now at FIGS. 13 and 14, a CT scanner 140 can be placed in front of radiotherapy system 70 (comprising a single C-arm 80 movably supporting two X-ray tubes 75 thereon), and can be indexed to isocenter 90, such that a calibrated CT scan can be performed, and then the patient shifted a precise amount, for treatment within the coordinate system.

See also FIGS. 15-18, where CT scanner 140 is placed in front of a radiotherapy system 70 comprising two C-arms 80, wherein each C-arm 80 movably supports one X-ray tube 75 thereon.

Image Guided Radiation Therapy

In the foregoing section, there is disclosed a small beam area, mid-voltage radiotherapy system with reduced skin dose, reduced scatter around the treatment volume, and improved overall accuracy. As disclosed therein, this system can provide improved radiation therapy to a patient.

In accordance with a further aspect of the present invention, and as will now hereinafter be discussed, the same system can be used for both radiation therapy and X-ray imaging, whereby to provide improved image guided radiation therapy for the patient. Thus, in this form of the present invention, a single x-ray beam can serve the functions of both radiation therapy and X-ray imaging, for the purpose of performing image guided radiation therapy.

More particularly, the present invention comprises the provision and use of a movable X-ray source and movable imaging detector diametrically opposed to the X-ray source and configured to move in concert with the X-ray source. The X-ray beam generated by the X-ray source may be a treatment mode X-ray beam for treating a tumor, or a lower energy imaging mode X-ray beam for imaging the treatment volume and/or for monitoring apparatus for configuring the X-ray beam (e.g., MLCs) and/or for monitoring the X-ray beam dose. The anatomy to be treated (e.g., a tumor inside a patient) can be imaged using the X-ray source in image mode and then positionally adjusted relative to the X-ray source (e.g., by moving the patient support table relative to the X-ray source) so that the anatomy to be treated is optimally aligned for subsequent treatment with the X-ray beam when the X-ray source is in treatment mode. Note that inasmuch as the same X-ray source is used for both imaging (and patient alignment) and treatment, the isocenter of the treatment X-ray beam can always be perfectly centered on the target tissue, i.e., by using the X-ray beam in imaging mode to identify the location of the target tissue and then aligning the patient with the isocenter of the treatment X-ray beam.

In general, guiding the placement of a radiation therapy treatment field, as it is conventionally practiced, generally involves one or more of the following steps:

(1) obtaining the location of the tumor via magnetic resonance imaging (MRI), positron emission tomography (PET) or X-ray computed tomography (CT), typically days or weeks prior to the treatment, using separate equipment in a separate room;

(2) marking the patient's body at the approximate location of the tumor (i.e., on the surface of the patient's skin) with ink marks or radio-opaque dots, or with masks placed on the surface of the patient, or with digital parameters;

(3) positioning the therapy beam (as represented by co-aligned light fields with cross-hairs, or isocentric lasers) over the ink marks or radio-opaque dots or masks, or located using the aforementioned digital parameters (e.g., data or voxel maps) prior to turning on the radiation therapy beam; and/or (4) optionally, inside the radiation therapy room, with the patient constrained on the patient support table, deploying a separate X-ray source and an X-ray imaging detector to obtain images to confirm that the tumor is located at the isocenter of the treatment beam, typically by using X-ray-visible landmarks from a separate system—however, because this imaging system is separated from the radiation treatment beam and its multi-leaf collimator (MLC), careful calibration and triangulation must be done to align the imaging beam with the radiation therapy beam and, even then, there is no independent confirmation that the leaflets of the MLC are set at the correct opening during radiation treatment.

Due to the very high energy—in excess of a million electron volts (MeV) employed by Gamma Knifes (1.2 MeV), liner accelerators (6 MeV), and proton beam (250 MeV)—these radiation beams cannot be used for imaging because of low image contrast. A separate, lower energy X-ray beam must be used for image guidance with these machines. The Gamma Knife is inherently unable to image due to its many large X-ray sources.

Thus, image-guided radiation therapy is not as accurate, practical or feasible as it might be with the current standards of practice using a Gamma Knife, a linear accelerator or a proton therapy beam, all of which require an independent means of imaging at much lower energy for good contrast.

Because of the use of different physical beam equipment, separated in time and space, there are inherent uncertainties in determining, qualitatively and quantitatively, where, and how well, the therapeutic radiation beam has been matched to the tumor under treatment. Using X-ray for both imaging and treatment purposes, from the same X-ray source device, overcomes these issues.

Thus, in one preferred form of the present invention, there is provided a novel method and apparatus for using an X-ray radiation treatment beam, in combination with an imaging device, to provide imaging shortly before, or during, a radiation therapy treatment sourced from the same therapeutic X-ray tube and patient position, in order to facilitate better localization, visualization and targeting of tumors, and to perform dose monitoring and verification, so as to enable precise treatment with minimal collateral damage of surrounding healthy organs, using one or more combinations of: (a) radiation therapy with a sharp-edged therapeutic X-ray beam positioned under the guidance of X-ray imaging, (b) enhanced X-ray visualization of a tumor or other target tissue using contrast agents, (c) drug treatment delivered through a catheter or syringe under the guidance of imaging, and (d) use of radiation-activated or ionization-activated chemotherapy drugs or catalysts with this device.

Figure 19:
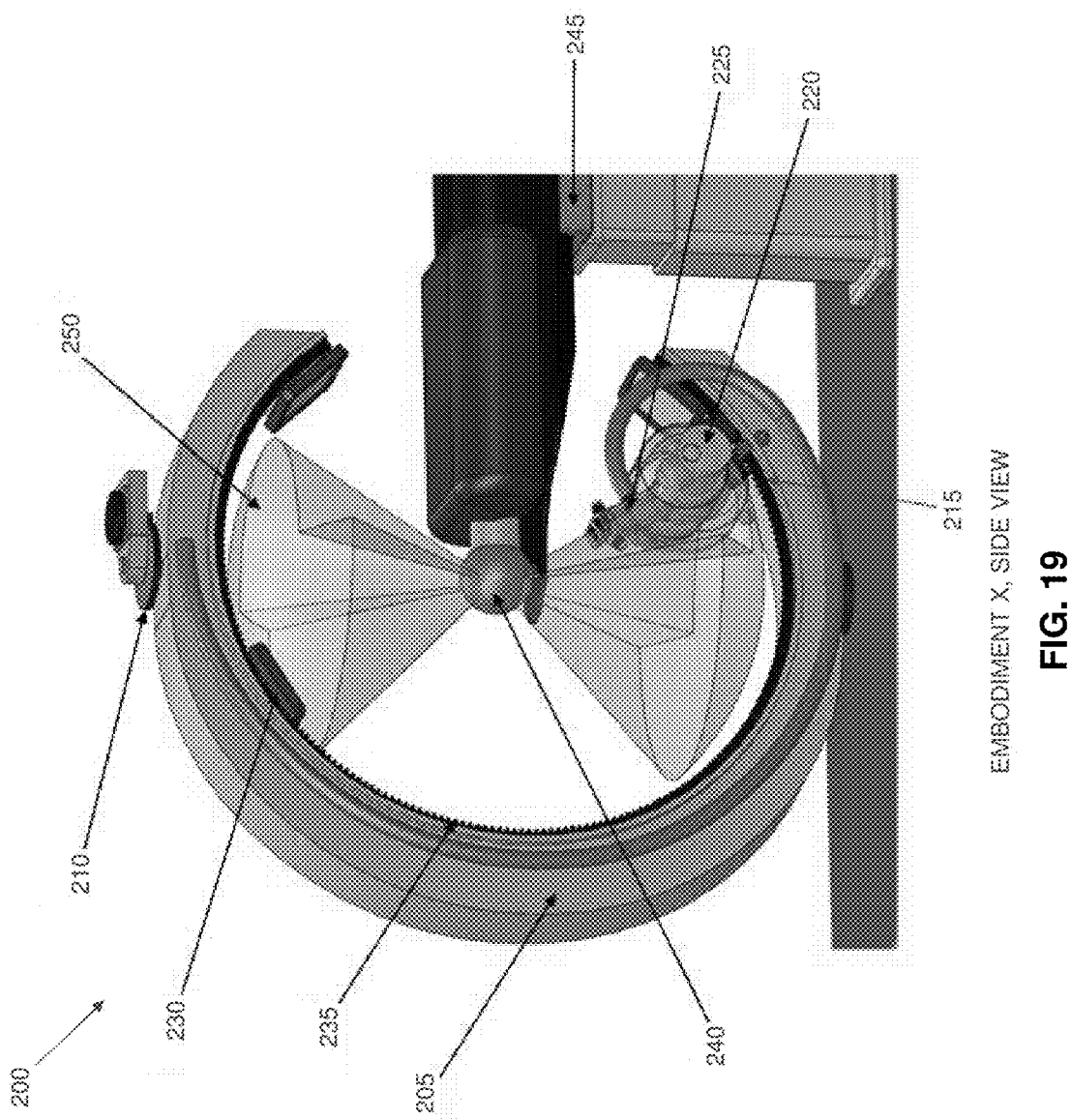
FIG. 19 is a schematic view showing another form of radiotherapy system formed in accordance with the present invention, wherein the radiotherapy system is configured to provide image guided radiation therapy.

Looking now at FIG. 19, there is shown an image-guided radiotherapy system 200 which comprises one preferred form of the present invention, wherein the image-guided radiotherapy system comprises a C-arm 205 mounted to a vertical axis bearing 210, wherein the C-arm carries an X-ray assembly 215 comprising an X-ray source 220 and an associated MLC 225 on one side, and an imaging detector 230 positioned diametrically across from X-ray assembly 215 on the other side of the C-arm. Both X-ray assembly 215 and imaging detector 230 can be moved in locked synchronization around a circular track 235, with the X-ray beam generated by X-ray source 220 passing through a treatment volume 240. Significantly, in accordance with the present invention, X-ray assembly 215 may be used for both radiation therapy and imaging (e.g., by using different electrical parameters on the same X-ray tube), thereby eliminating any misalignment which might be caused by the separation of the therapy beam and diagnostic beam in space and/or time. Imaging detector 230 is preferably configured to allow both 2D and 3D images of the treatment volume, as well as 2D images of the MLC opening, to be acquired, viewed, computer processed and recorded, before, during and/or after the radiation treatment.

In one preferred form of the invention, the image-guided radiotherapy system 200 is a small beam area, mid-voltage radiotherapy system with reduced skin dose, reduced scatter around the treatment volume, and improved overall accuracy, such as the novel radiotherapy system disclosed above and shown in FIGS. 5-18 (e.g., a radiotherapy system comprising an X-ray tube operating at 100 to 800 kVp, and preferably at 150 kVp to 600 kVp, during a radiation therapy mode and providing X-ray beams of approximately 50 mm diameter or less and configured to move the entrance beam footprint on the body during irradiation to any arbitrary sequential position set that has been predetermined to limit the intervening tissue dose rate at any one location to a safe level, such that the sum of the skin area traversed during treatment is approximately 20 to 100 times the beam area).

In one preferred form of the invention, prior to operating the X-ray tube in the aforementioned therapy mode, the X-ray tube is first operated at a lower power imaging mode (e.g., 30 kVp to 150 kVp) so as to allow the target tissue to be imaged and then aligned (e.g., by moving the patient bed)

with the isocenter of the treatment X-ray beam. In this way, the radiotherapy system can ensure that the tissue to be therapeutically irradiated is properly targeted by the treatment X-ray beam.

By way of example but not limitation, image guidance of the radiation therapy may be performed using one or more of the following approaches:

(1) Immediately before the radiation treatment, after the patient has been constrained on the patient support table 245, with the treatment volume 240 initially positioned approximately at the isocenter of the C-arm, a 3D CT volume image is obtained, by scanning with X-ray source 220 (with the leaflets of MLC 225 appropriately opened to a line opening) and imaging detector 230 around treatment volume 240. The 3D CT volume image allows the tumor under treatment to be confirmed by comparing the 3D CT volume image with previous MRI or CT images obtained in an earlier diagnostic phase. With the latest updated 3D positional measurement obtained by scanning with X-ray source 220 and imaging detector 230, the tumor may be accurately placed at the isocenter of C-arm 205 by fine adjustment of patient support table 245. Imaging detector 230 may be a 2D "flat panel" detector as shown in FIG. 19, or a classic CT "arc-type" detector, or both.

(2) Immediately before the radiation treatment, after the patient has been constrained on patient support table 245, with treatment volume 240 initially positioned approximately at the isocenter of C-arm 205, and with the leaflets of MLC 225 fully opened, and 2D imaging detector 230 diametrically opposed to X-ray assembly 215, a catheter or a syringe may be employed to inject contrast agents, or chemotherapy drugs, or drugs containing fluorescence agents, or radiation-activated catalysts or drugs, into the patient. A sequence of fluoroscopic cine pictures may then be obtained (using X-ray source 220 and imaging detector 230) at a frame rate of between about 1 Hz and about 25 Hz, to enable the physician to observe the perfusion of the contrast agents or drugs or catalysts through the vasculature surrounding the tumor, allowing the tumor under treatment to be identified. With the latest updated 3D positional measurement obtained by scanning with X-ray source 220 and imaging detector 230, the tumor may be accurately placed at the isocenter of C-arm 205 by fine adjustment of patient support table 245.

In one preferred form of the present invention, when X-ray source 220 is operating in imaging mode, the X-ray source is operated in pulse mode, with pulse duration in the millisecond range and pulse separation in the millisecond range. In one preferred form of the invention, the pulse duration is approximately 1-10 milliseconds at approximately 20 kW when X-ray source 220 is operating in pulse mode.

Once the treatment volume is confirmed and its position is adjusted so as to be at the isocenter of C-arm 205, a simulation scan can be performed, with the radiation source (i.e., X-ray source 220) operating at a low dose level (e.g., at a fraction of the radiation therapy level) which is suitable for obtaining images but not high enough to cause radiation damage. The purpose of the simulation scan is to confirm that the programmed treatment sequence is exactly the same as the prescribed radiation treatment. During this simulation scan, X-ray source 220 and the imaging detector 230 are traced through one or more sectors of spherical scan surfaces 250, with the leaflets of MLC 225 being dynamically set at their prescribed openings at different scan positions for the purpose of confining the radiation to within the treatment volume 240, and to spare the healthy organs outside the treatment volume. During the simulation scan, a series of 2D images are obtained by imaging detector 230. The series of 2D images can serve two functions: (1) to independently confirm that the actual openings of the leaflets of MLC 225 are identical to the prescribed openings at all scan locations, and (2) to obtain a series of calibrated readings of the radiation dose exiting the far side of the patient, so that the total radiation dose delivered to the treatment volume, as well as to the patient, can be computed and compared against the prescribed radiation dose. With suitable calibration, the data in the series of 2D images thus obtained in this simulation scan can be used to predict and confirm that the correct dose will be correctly delivered in the subsequent "real treatment phase" (i.e., when the radiation beam is operating at full power).

Following positive verification of the correct operation of all of the components for this simulation scan, and within a time delay of only several seconds, the scan sequence is repeated with all operating parameters identical to those in the simulation scan, except: (1) the radiation therapy beam is operated at full power (i.e., at 100 kVp to 800 kVp, and preferably at 300 kVp to 500 kVp), and (2) a neutral density filter is inserted in front of imaging detector 230 to reduce the dose intensity hitting the imaging detector, to prevent signal saturation and damage to the imaging detector. During the radiation treatment scan, a series of 2D images are again collected by imaging detector 230 and analyzed in real time, for confirmation that: (1) the actual openings of the leaflets of MLC 225 are identical to the prescribed openings for the leaflets at all scan locations, and (2) the measured dose exiting from the patient is consistent with the prescribed treatment dose. If the deviation of either the MLC opening or the radiation dose exceeds a prescribed maximum threshold, the radiation treatment is aborted and an alarm is sounded. All operating parameters are saved to the patient treatment record.

If desired, X-ray source 220 may be switched in quick succession between operating in radiation therapy mode and imaging mode (e.g., in the range of about 1 Hz to about 60 Hz), with X-ray source 220 operating at different energy levels, and at various duty cycles, including classic CT loading.

In one preferred form of the invention, image-guided radiotherapy system 200 comprises a mid-voltage radiotherapy system which provides a small beam area having reduced scatter around the treatment volume and which is appropriately moved (i.e., scanned) about the patient's anatomy so as to provide reduced skin dose while delivering a therapeutic radiation dose to the target tissue (i.e., the treatment volume), such as the novel radiotherapy system discussed above (e.g., a radiotherapy system comprising an X-ray tube operating at 100 to 800 kVp for providing X-ray beams of approximately 50 mm diameter or less and configured to move the entrance beam footprint on the body during irradiation to any arbitrary sequential position set that has been predetermined to limit the intervening tissue dose rate at any one location to a safe level, such that the sum of the skin area traversed during treatment is approximately 20 to 100 times the beam area).

Figure 20:
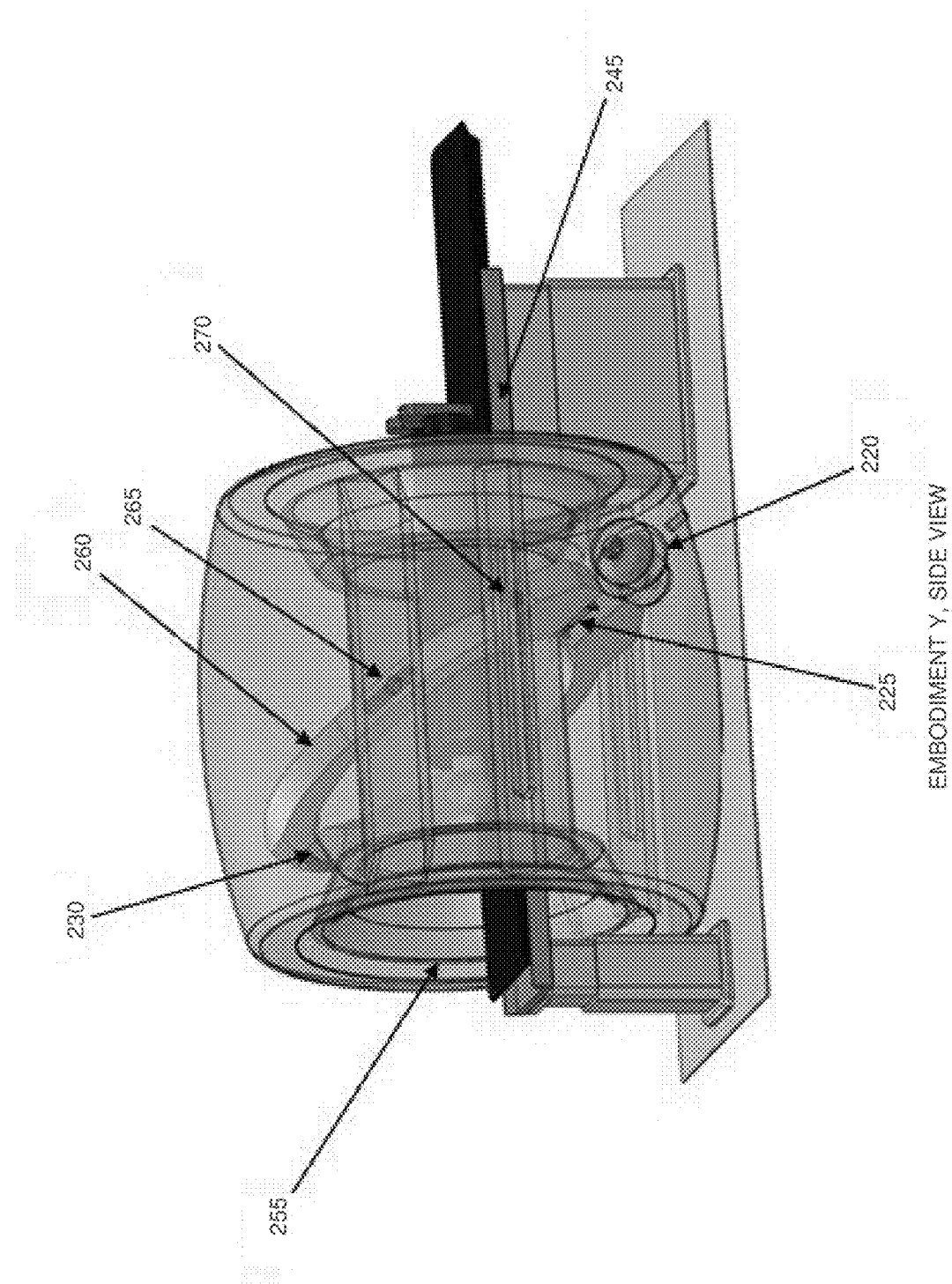

FIGS. 20 and 21 are schematic views showing another image-guided radiotherapy system formed in accordance with the present invention, wherein the image-guided radiotherapy system comprises of an outer barrel 255 and an inner O-ring 260. Outer barrel 255 can be rotated around a horizontal axis, carrying inner O-ring 260. Inner O-ring 260 is mounted on the inside of outer barrel 255 through a pivot slot 265 and a motor-driven rack-and-pinion bearing 270. By controlling the linear position of rack-and-pinion bearing 270, the angle of tilt of inner O-ring 260 may be scanned through an angular range. Using a combination of the rotation of outer barrel 255 and the tilting of inner O-ring 260, a 3D scan volume may be traced out so as to perform radiation therapy on a patient disposed within outer barrel 255 and inner O-ring 260. In this form of the invention, inner O-ring 260 carries an X-ray source 220 and an associated MLC 225 fixed to one side of inner O-ring 260, and an imaging detector 230 fixed to the opposite side of inner O-ring 260, diametrically across from X-ray source 220 and MLC 225.

With respect to the construction shown in FIGS. 20 and 21, the operations of X-ray source 220, MLC 225, imaging detector 230, outer barrel 255 and inner O-ring 260 for image guidance, simulation scan and final therapy scan are exactly the same as discussed above with respect to the apparatus of FIG. 19.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A system for image-guided radiotherapy, the system comprising:
   a gantry;
   at least one X-ray tube movably mounted to the gantry, wherein the at least one X-ray tube operates at 350 kVp to 800 kVp when providing radiotherapy; and
   at least one detector disposed opposite the at least one X-ray tube, the at least one detector being configured to permit selective imaging using the at least one X-ray tube;
   wherein the gantry is configured to move the at least one X-ray tube about a treatment volume such that X-rays emitted from the at least one X-ray tube are continuously directed at the treatment volume from any position relative to the treatment volume, and further wherein the gantry is configured such that when the treatment volume is disposed at the center of a spherical projection, the gantry is able to move the at least one X-ray tube so as to direct the X-rays emitted from the at least one X-ray tube at the treatment volume from any position on an inside surface of the spherical projection.

2. A system according to claim 1 wherein the at least one detector comprises a two dimensional imaging detector configured to permit both selective imaging and selective dose measurement.

3. A system according to claim 2 wherein the two dimensional imaging detector has a configuration selected from the group consisting of (i) a plate detector having dimensions in the range of approximately 15 cm to approximately 30 cm and (ii) a CT arc-type detector.

4. A system according to claim 2 wherein the at least one X-ray tube and the two dimensional imaging detector are arranged on two opposite sides of the gantry, and further wherein the gantry comprises a rotatable arcuate structure, with the patient under treatment at the center of the rotatable arcuate structure, around which the at least one X-ray tube and the two dimensional imaging detector are scanned.

5. A system according to claim 4 wherein the rotatable arcuate structure comprises a gimbal.

6. A system according to claim 4 wherein the at least one X-ray tube may be operated in two modes:
   (a) a radiation therapy mode, with the energy of the photon beam being in the range of 350 kVp to 800 kVp; and
   (b) an imaging mode, with the energy of the photon beam being in the range of 30 kVp-150 kVp.

7. A system according to claim 6 wherein, when the at least one X-ray tube is operated in the imaging mode, the at least one X-ray tube is operating in pulse mode, with pulse duration in the millisecond range, and pulse separation in the millisecond range.

8. A system according to claim 7 wherein, when the at least one X-ray tube is operated in the imaging mode, the at least one X-ray tube is operating in pulse mode, with pulse duration of 1-10 milliseconds, at approximately 20 kW.

9. A system according to claim 6 wherein the at least one X-ray tube may be switched between operating in the radiation therapy mode or the imaging mode in quick succession, in the range of about 1 Hz to about 60 Hz, at different energy levels, and at various duty cycles.

10. A system according to claim 4 wherein the at least one X-ray tube may also serve as the activation agent for radio-sensitive drugs or catalysts.

11. A radiotherapy system according to claim 4 wherein the imaging detector array may be operated in four modes using the X-ray emitted from the at least one X-ray tube:
   (a) a 3D imaging mode using computerized tomographic reconstruction methods while both the at least one X-ray tube and the two dimensional imaging detector are scanned around the patient;
   (b) a 2D movie snapshot imaging mode for determining the exact beam profile and the positions of a collimating aperture for the at least one X-ray tube, synchronously with the operation of the at least one X-ray tube and a collimating aperture for the at least one X-ray tube, at different scan positions, for the purpose of verifying the correct masking of the radiation beam by the collimating aperture to confine the radiation beam to the area of interest and to provide active image-guided control, by reconfiguring of the collimating aperture, to minimize unneeded radiation damage to surrounding organs;
   (c) a 2D movie snapshot imaging mode with the images being captured in quick succession, with integration time in the 1,000 to 10,000 microsecond range, and repetition rate in the range of 1 Hz to 60 Hz, to image the flow of a contrast enhanced agent or drug or blood flow around the area under diagnosis and treatment, as in angiography; and
   (d) a 2D movie snapshot imaging mode with the images being captured in quick succession, with integration time in the 1/10 to 10,000 microsecond range, and repetition rate in the range of 1 Hz and 60 Hz, to calculate the intensity of the radiation dosage delivered to the tumor.

12. A system according to claim 11 wherein a filter is positioned between the at least one X-ray tube and the two dimensional imaging detector.

13. A system according to claim 12 wherein the filter comprises at least one from the group consisting of a neutral density filter and a spectral shaping filter.

14. A system according to claim 4 wherein the at least one X-ray tube and the two dimensional imaging detector are operated in a fluoroscopy imaging mode so as to generate a movie which may be used (i) to assist in the guidance of catheters or injections, (ii) to assist in the visual confirmation of the delivery of drugs, contrast agents or radio-activated catalysts, and (iii) to assess the operational status of a collimating aperture.

15. A system according to claim 1 wherein the system is configured such that the at least one X-ray tube and the at least one detector may be used to construct a three-dimensional model of the treatment volume.

16. A system according to claim 15 wherein the system is configured to use the three-dimensional model of the treatment volume to ensure that the X-ray emitted by the at least one X-ray tube is continuously directed at the treatment volume from any position relative to the treatment volume.

\* \* \* \* \*